US008338137B2

(12) United States Patent
Rokbi et al.

(10) Patent No.: US 8,338,137 B2
(45) Date of Patent: *Dec. 25, 2012

(54) TYPE 5 AND TYPE 8 CAPSULAR POLYSACCHARIDES OF OVERPRODUCING S. AUREUS STRAINS

(75) Inventors: Bachra Rokbi, Lyons (FR); Claude Meric, Lyons (FR); Noelle Mistretta, Sain Bel (FR); Philippe Talaga, Sainte Consorce (FR); Olivier Adam, Lentilly (FR)

(73) Assignee: Sanofi Pasteur S.A., Lyons (FR)

( * ) Notice: Subject to any disclaimer, the term of this patent is extended or adjusted under 35 U.S.C. 154(b) by 1586 days.

This patent is subject to a terminal disclaimer.

(21) Appl. No.: 11/687,714

(22) Filed: Mar. 19, 2007

(65) Prior Publication Data

US 2011/0052624 A1 Mar. 3, 2011

Related U.S. Application Data

(60) Provisional application No. 60/746,670, filed on May 8, 2006.

(30) Foreign Application Priority Data

Mar. 31, 2006 (FR) ..................... 06 02795

(51) Int. Cl.
*C12P 21/04* (2006.01)
*C12P 19/00* (2006.01)
*C12P 21/06* (2006.01)
*A01N 63/00* (2006.01)
*A61K 39/09* (2006.01)
*A61K 45/00* (2006.01)

(52) U.S. Cl. ....... 435/72; 435/70.1; 435/71.2; 435/69.1; 435/883; 424/282.1; 424/237.1; 424/93.42

(58) Field of Classification Search .................. None
See application file for complete search history.

(56) References Cited

U.S. PATENT DOCUMENTS

| 6,045,805 | A | 4/2000 | Moreau | |
|---|---|---|---|---|
| 6,472,506 | B1* | 10/2002 | Moreau et al. | 530/322 |
| 7,521,221 | B2* | 4/2009 | Lee et al. | 435/252.3 |
| 7,863,013 | B2* | 1/2011 | Rokbi et al. | 435/34 |
| 2007/0031939 | A1* | 2/2007 | Rokbi et al. | 435/85 |
| 2007/0166803 | A1* | 7/2007 | Lee et al. | 435/101 |
| 2010/0184160 | A1* | 7/2010 | Lee et al. | 435/101 |
| 2010/0330656 | A1* | 12/2010 | Rokbi et al. | 435/252.1 |
| 2011/0052624 | A1* | 3/2011 | Rokbi et al. | 424/197.11 |

FOREIGN PATENT DOCUMENTS

| FR | 2884830 | * | 10/2006 |
|---|---|---|---|
| WO | 03/061558 | A2 | 7/2003 |
| WO | 2004/043407 | A2 | 5/2004 |
| WO | 2004/080490 | A2 | 9/2004 |
| WO | 2006/114500 | A2 | 11/2006 |
| WO | 2007/062366 | A2 | 5/2007 |

OTHER PUBLICATIONS

O'Riordan et al, Clinical Microbiology Reviews, Jan. 2004, 17/1:218-234.*
Robbins et al, Am. Heart J., 2004, 147:593-598.*
Hamilton, Carol M., et al., "New Method for Generating Deletions and Gene Replacements in *Escherichia coli*," Journal of Bacteriology, Sep. 1989, pp. 4617-4622, vol. 171, No. 9, American Society for Microbiology.
Sau Subrata et al.,"Molecular Characterization and Transcriptional Analysis of Type 8 Capsule Genes in *Staphylococcus aureus*," Journal of Bacteriology, Mar. 1997, pp. 1614-1621, vol. 179, No. 5, American Society for Microbiology.
Jones, Christopher, "Revised Structures for the Capsular Polysaccharides from *Staphylococcus aureus* Types 5 and 8 Components of Novel Glycoconjugate Vaccines," Carbohydrate research, May 2, 2005, pp. 1097-1106, vol. 340, No. 6.
Luong Thanh et al, "Regulation of *Staphylococcus aureus* Capsular Polysaccharide Expression by agr and sarA," Infection and Immunity, Feb. 2002, pp. 444-450, vol. 70, No. 2, American Society for Microbiology.
Link, Andrew J., et al., "Methods for Generating Precise Deletions and Insertions in the Genome of Wild-Type *Escherichia coli*: Application to Open Reading Frame Characterization," Journal of Bacteriology, Oct. 1997, pp. 6228- 6237, vol. 179, No. 20, American Society for Microbiology.
Dassy, B., et al., "Production of Type 5 Capsular Polysaccharide by *Staphylococcus aureus* Grown in a Semi Synthetic Medium," Journal of General Microbiology, 1991, pp. 1155-1162, vol. 137.
Lee, Jean C., et al., "Effects of In Vitro and In Vivo Growth Conditions on Expression of Type 8 Capsular Polysaccharide by *Staphylococcus aureus*," Infection and Immunity, May 1993, pp. 1853-1858, vol. 61, No. 5, American Society for Microbiology.
Ouyang, Shu, et al., "Promoter Analysis of the Cap8 Operon, Involved in Type 8 Capsular Polysaccharide Production in *Staphylococcus aureus*," Journal of Bacteriology, Apr. 1999, pp. 2492-2500, vol. 181, No. 8, American Society for Microbiology.
Poutrel, B, et al., "Effects of Culture Conditions on Production of Type 5 Capsular Polysaccharide by Human and Bovine *Staphylococcus aureus* Strains," Clinical and Diagnostic Laboratory Immunology, Mar. 1995, pp. 166-171, vol. 2, No. 2, American Society of Mircrobiology.
Taylor, D., et al., "Amino Acid Requirements for the Growth and Production of Some Exocellular Products of *Staphylococcus aureus*," Journal of Applied Bacteriology, 1989, pp. 319-329, vol. 66.
Luong, Thanh T., et al., "Overproduciton of Type 8 Capsular Polysaccharide Augments *Staphylococcus aureus* Virulence," Infection and Immunity, Jul. 2002, pp. 3389-3395, vol. 70, No. 7 American Society of Microbiology.
Stringfellow, W.T., et al., "*Staphylococcus aureus* Growth and Type 5 Capsular Polysaccharide Production in Synthetic Media," Applied and Environmental Microbiology, Feb. 1991, pp. 618-621, vol. 57, No. 2, American Society for Microbiology.

* cited by examiner

Primary Examiner — Nita M Minnifield
(74) Attorney, Agent, or Firm — McDonnell Boehnen Hulbert & Berghoff LLP

(57) ABSTRACT

The invention relates to the type 5 and type 8 capsular polysaccharides produced by overproducing *S. aureus* strains, and also to the immunogenic compositions and the vaccines comprising said capsular polysaccharides.

19 Claims, 8 Drawing Sheets

GROUPS

Figure 1:
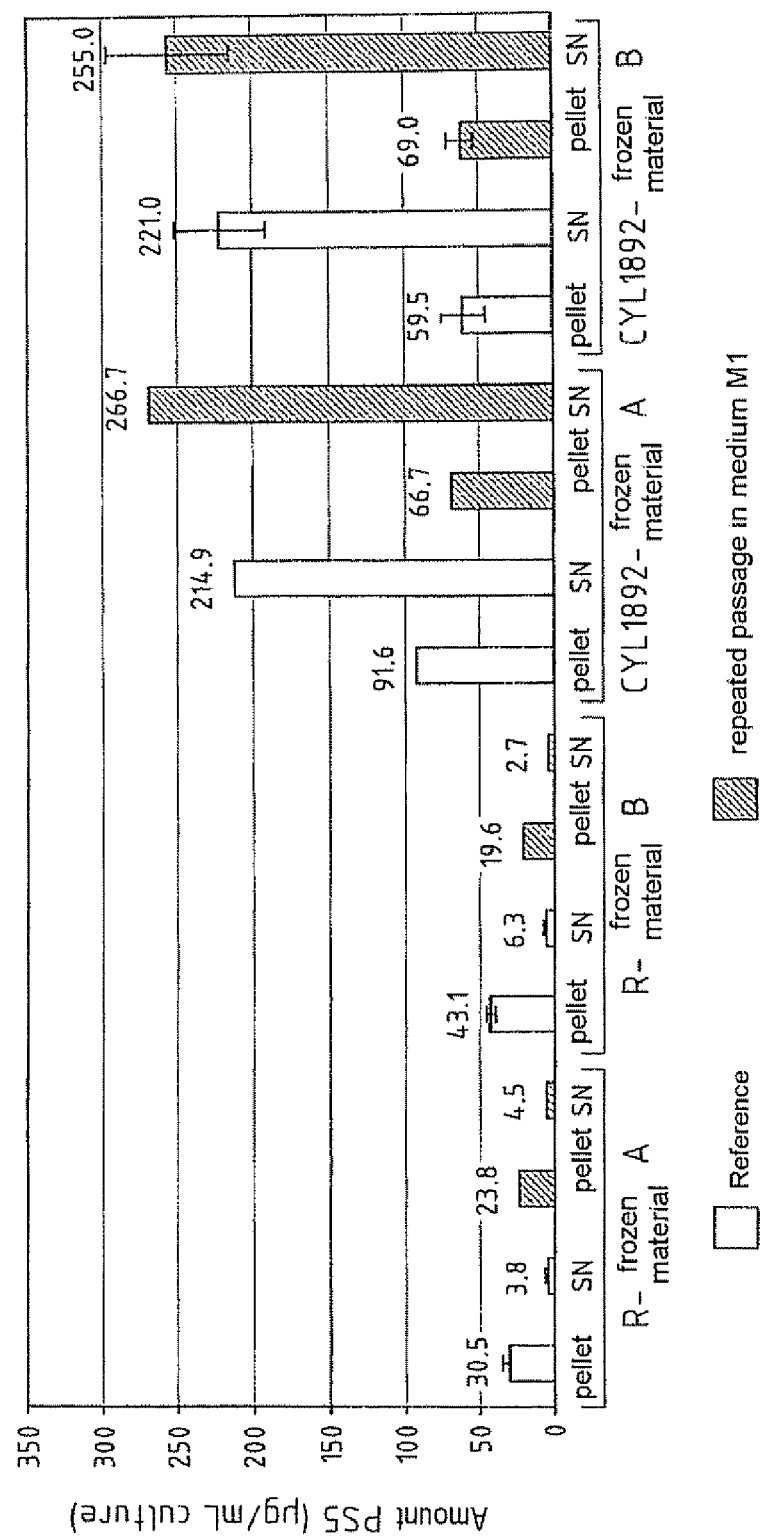

- rEPA + PS8 from Becker, native
- rEPA + PS8 from CYL770, depolymerized (70 kDa)
- PS8 - rEPA batch 3 (Becker)
- PS8 - rEPA batch 4 (Becker)
- PS8 - rEPA batch 5 (depolymerized CYL770)
- PS8 - rEPA batch 6 (depolymerized CYL770)
- rEPA + PS8 from CYL770 native CP8 culture supernatant CYL after de-O-acetylation (chemical shift ppm)

CP8 culture supernatant CYL before de-O-acetylation (chemical shift ppm)

Figure 5(a)

CP8, Becker bacterial pellet after de-O-acetylation (chemical shift ppm)

CP8, Becker bacterial pellet before de-O-acetylation (chemical shift ppm)

CP5 culture supernatant mutant strain CYL1892

(chemical shift ppm)

CP5 bacterial pellet wild-type strain (chemical shift ppm)

Figure 7(a). Evaluation and comparison of the anti- PS5 IgM responses induced in mice with the PS5-rEPA and rPS5-rEPA conjugates
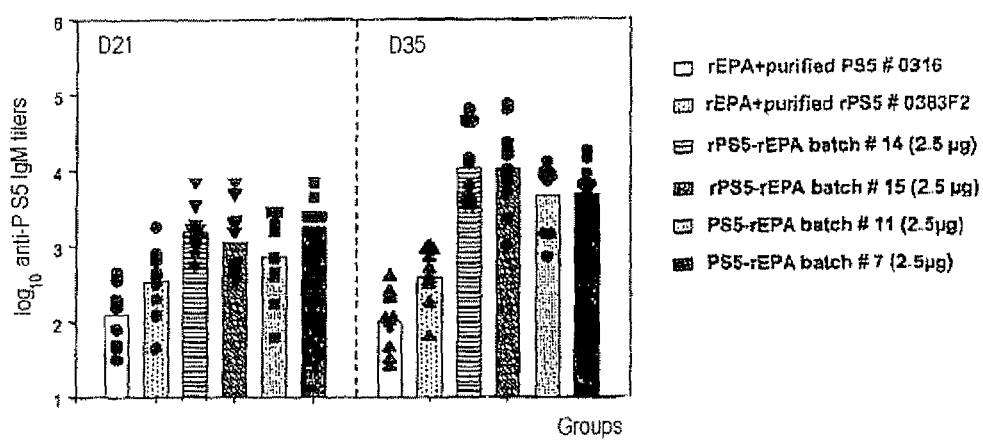
Figure 7(b). Evaluation and comparison of the anti- PS5 IgG responses induced in mice with the PS5-rEPA and rPS5-rEPA conjugates
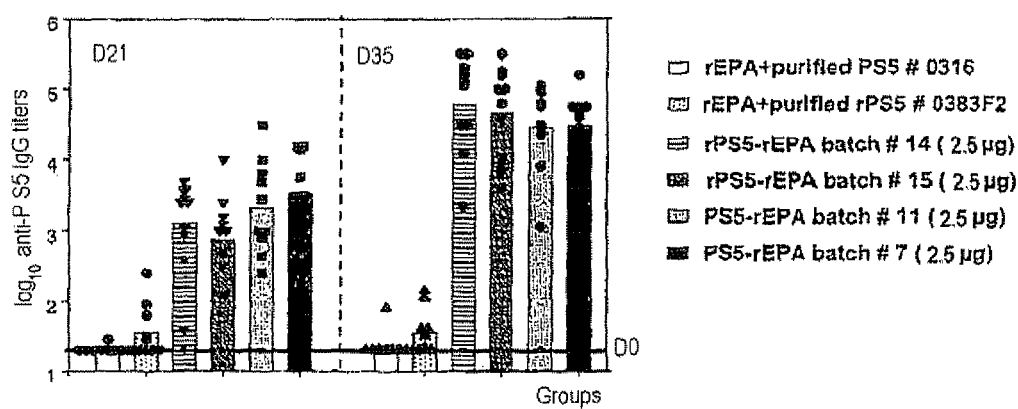

TYPE 5 AND TYPE 8 CAPSULAR POLYSACCHARIDES OF OVERPRODUCING *S. AUREUS* STRAINS

This application claims the benefit of priority of French application 0602795, filed Mar. 31, 2006 and U.S. Provisional application 60/746,670, filed May 8, 2006.

The invention relates to the type 5 and type 8 capsular polysaccharides produced by overproducing *S. aureus* strains, in particular by the CYL1892 and CYL770 strains, and also to the use thereof for immunization against an infection with an *S. aureus* serotype 5 and/or 8 strain.

The *S. aureus* strains comprise a peptidoglycan wall and possibly polysaccharides bound to the outer surface of the latter, which form a more or less thick structure called capsule or glycocalyx. These capsular polysaccharides are formed by the assembly of repeating units, the constituents and the bonds of which are defined and are characteristic of the bacterial species. These repeating units contain the epitopes and the structures that determine antigenicity.

The discovery of serologically distinct capsular polysaccharides at the surface of clinical isolates of *S. aureus* has led to their role in the virulence of these strains being studied. The serotyping of *S. aureus* strains has shown that serotypes 5 and 8 are responsible for the large majority of human infections.

The development of a vaccine against an infection with *S. aureus* represents major stakes because of the seriousness of the complications engendered and the ever increasing emergence of strains resistant to current antibiotics. The development of a vaccine that protects against infections with *S. aureus* serotype 5 and serotype 8 (T5 and T8) strains would make it possible to protect an individual against an infection with 85 to 90% of *S. aureus* strains.

An important obstacle to the development of a vaccine against *S. aureus* based on the capsular antigens is the low productivity, which is variable according to the culture conditions, of the wild-type strains which express T5 and T8.

The inventors have demonstrated, surprisingly, that the wild-type *S. aureus* strains which have been genetically modified to produce capsular polysaccharide (PS) in large amounts can be advantageously used to produce polysaccharides of interest.

The inventors have in fact shown that the *S. aureus* T5 and T8 strains, modified by genetic recombination so as to obtain strains that overproduce the capsular PS, are capable of producing, in large amounts in the culture supernatant, a capsular polysaccharide which, although different from the wild-type PS, induces a humoral response comprising antibodies against the wild-type capsular PS.

A subject of the present invention is therefore an immunogenic composition comprising a T8 and/or T5 capsular polysaccharide of an overproducing *S. aureus* T8 and/or T5 strain, respectively.

According to a particular embodiment, said composition comprises a T5 capsular polysaccharide of an *S. aureus* CYL1892 strain.

According to another embodiment, said composition comprises a T8 capsular polysaccharide of an *S. aureus* CYL770 strain.

According to a particular embodiment, said composition comprises a T5 capsular polysaccharide of an *S. aureus* CYL1892 strain and a T8 capsular polysaccharide of an *S. aureus* CYL770 strain.

According to a particular embodiment, said immunogenic composition comprises a conjugate comprising a T8 and/or T5 capsular polysaccharide of an overproducing *S. aureus* strain, bound to a carrier protein.

According to a particular embodiment, said conjugate comprises a T8 capsular polysaccharide of the CYL770 strain.

According to another embodiment, said conjugate comprises a T5 capsular polysaccharide of the CYL1892 strain.

According to a particular embodiment, said immunogenic composition comprises a conjugate comprising a T8 capsular polysaccharide of the CYL770 strain and a conjugate comprising a T5 capsular polysaccharide of the CYL1892 strain.

According to a particular embodiment, said conjugates comprise a fractionated capsular polysaccharide.

According to a particular embodiment, the carrier molecule of the conjugate according to the present invention is *Pseudomonas aeruginosa* exotoxin A.

According to another aspect, the present invention relates to a conjugate comprising a T8 or T5 capsular polysaccharide of an overproducing *S. aureus* strain, bound to a carrier protein, advantageously *Pseudomonas aeruginosa* exotoxin A. According to one embodiment, said PS is fractionated.

According to a particular embodiment, said conjugate comprises a capsular polysaccharide of the *S. aureus* CYL1892 strain.

According to another embodiment, said conjugate comprises a capsular polysaccharide of the *S. aureus* CYL770 strain.

Said PSs are preferably fractionated before being conjugated.

According to another aspect, the present invention relates to a type 5 capsular polysaccharide of the *S. aureus* CYL1892 strain. This polysaccharide is advantageously in isolated or purified form.

According to another aspect, the present invention relates to the use of a conjugate as defined above, for the manufacture of an immunogenic composition for immunization against *S. aureus* infections.

According to another aspect, the present invention relates to a method of producing T5 capsular polysaccharide, comprising the steps consisting in:

a) culturing an overproducing *S. aureus* strain,
b) inactivating the culture thus produced, and
c) recovering the T5 capsular polysaccharide from the supernatant.

According to a particular embodiment of the method according to the invention, the overproducing strain is the CYL1892 strain.

The invention will be described in greater detail in the description which follows, with reference to FIGS. 1 to 6.

The term "*S. aureus* strain(s)" is intended to mean any *S. aureus* strain expressing a capsule or a microcapsule comprising a T5 and/or T8 polysaccharide. Mention may be made, by way of nonlimiting example, of the Newman (T5), Reynolds (T5), Lowenstein (T5), Becker (T8) and Wright (T8) strains. The strains advantageously used in the context of the present invention are the Reynolds and Becker strains.

In the context of the present invention, the term "overproducing strain" is intended to mean an *S. aureus* strain which has been genetically modified so as to produce at least 10, advantageously at least 20, times more capsular polysaccharide by weight, per unit volume, in the culture supernatant, than the parent strain from which it is derived when the two strains are cultured under the same culture conditions.

The amount of capsular polysaccharide produced can be determined by the ELISA method as described in example 1.

A "genetically modified" strain is an *S. aureus* strain whose genome has been modified by genetic engineering so as to increase its capsular polysaccharide production capacity. By way of example illustrating an appropriate genetic modification, mention may be made of the modification of *S. aureus* strains by replacement, by homologous recombination, of the principal promoter of the cap5 or cap8 operon with a strong principal promoter of another strain, such as the principal promoter of the cap1 operon of the *S. aureus* M strain. The method of gene insertion by homologous recombination is described in detail in the article by A. J. Link et al (J. of Bacteriology. October 1997, p. 6228-6237) and its specific application to the production of an overproducing *S. aureus* strain is described in detail in the article by T. T. Luong et al (Infection and Immunity, July 2002, p. 3389-3395). Reference can thus be made to these articles for further details regarding the operating conditions that can be used. This same method can also be used to construct a recombinant strain overproducing the T5 capsular polysaccharide. To do this, it may be necessary to adjust certain parameters, the homologous recombination being more or less readily carried out according to the starting strain. By way of example, an overproducing Reynolds CYL1892 strain in which the principal promoter of the cap5 operon has been replaced, by homologous recombination, with the principal promoter of the cap1 operon of the *S. aureus* M strain could be produced by means of the method of Luong et al., into which the following modifications were introduced: the homologous sequences were replaced with equivalent homologous sequences of the Reynolds strain, and the pCL52.2 plasmid was replaced with the pCL10 plasmid containing a thermosensitive origin of replication and comprising a cat marker (chloramphenicol acetyl tranferase conferring resistance to chloramphenicol). Briefly, a DNA fragment of approximately 1 kb containing the cap5 ORF of the Reynolds strain, fused to a fragment of approximately 250 bp containing the Pcap1 promoter, is constructed by the overlapping PCR technique. A DNA fragment of approximately 1 kb containing the sequence upstream of the cap5A gene is amplified by PCR from the genome of the Reynolds strain. The two fragments are then cloned into the pCL10 plasmid carrying a thermosensitive origin of replication and containing a cat marker such that the Pcap5 promoter is replaced with the Pcap1 promoter. The plasmid thus constructed is then electroporated into an RN4220 strain and then introduced by transduction using the bacteriophage 52 into the Reynolds strain. The temperature sensitivity of the origin of replication of the plasmid then makes it possible to promote the homologous recombination by blocking its replication while at the same time applying a selection with chloramphenicol.

The term "CYL770 strain" denotes the overproducing *S. aureus* strain obtained from a wild-type Becker strain (CIP103314) in which the promoter of the cap8 operon has been replaced with the strong promoter of the cap1 operon of the *S. aureus* M strain, as described by Luong and Lee (2002 *Infect. Immun.* 70: 3389-3395).

The term "CYL1892 strain" denotes the overproducing *S. aureus* strain obtained from a Reynolds strain (CIP 103313) in which the promoter of the cap5 operon has been replaced with the strong constitutive promoter of the cap1 operon of the *S. aureus* M strain, according to the method described by Luong and Lee (2002 *Infect. Immun.* 70: 3389-3395) comprising the modifications described above.

The inventors have also demonstrated that the overproducing *S. aureus* strains, in particular the CYL770 and CYL1892 strains, exhibit a high genetic stability. The term "high genetic stability" is intended to mean the property of the strains to conserve their capacity for overproduction after at least 25 passages on a culture medium suitable for culturing capsulated *S. aureus* strains, as measured by the test described in example 1.

Furthermore, the inventors have shown that the capsular polysaccharide produced by the overproducing *S. aureus* strains (hereinafter referred to as rPS) exhibit physicochemical characteristics different from those of the PS produced by the corresponding wild-type strain (hereinafter referred to as wtPS). The terms "PS8" and "PS T8" are used indifferently in the context of the present application to denote a serotype 8 capsular polysaccharide. Similarly, the terms "PS5" and "PS T5" are used indifferently in the context of the present application to denote a serotype 5 capsular polysaccharide.

The rPS T8 polysaccharide has a much higher average molecular weight than the corresponding wtPS, i.e. 250 kDa versus 150 kDa.

The rPS T5 polysaccharide has a much higher average molecular weight than the corresponding wtPS, i.e. 150 kDa versus 50 kDa. Furthermore, unlike wtPS T5, which remains bound to the bacterial wall, the inventors have shown that rPS T5 is mainly released into the culture supernatant.

The inventors have also observed that the rPSs exhibit properties of adsorption onto a plastic surface that are different from those of the wtPSs. Anti-PS8 polyclonal antibodies have been generated in rabbits by repeated injections of various T8 strains (Becker, Wright and CYL770), cultured beforehand in M1 medium. The anti-PS8 antibody titers of these sera were evaluated by ELISA using various PS8s (purified from the Becker, Wright or CYL770 strains) as adsorption antigen. The results showed that the anti-PS8 polyclonal serum, generated from the Becker strain, exhibits a high anti-PS8 antibody titer. This titer is similar, whether evaluated on the PS8 of the Becker strain or on the PS8 of the Wright strain. On the other hand, a low anti-PS8 titer is observed when the latter is evaluated with adsorbed PS8 which has been purified from the CYL770 strain. The same results were obtained for the sera generated from the Wright or CYL770 strains.

In order to verify that the weak recognition of the PS8 of CYL770 by the various sera was due to a reduced capacity of this rPS8 to bind to the treated plastic of an ELISA plate, and not to a difference in recognition of the PS8 itself, the three sera were titered by ELISA on rPS8 of CYL770 conjugated to rEPA, it being obligatory for the presence of the carrier protein to greatly improve the adsorption. Under these adsorption conditions, the anti-PS8 polyclonal sera generated from the 3 different T8 strains very strongly recognize the rPS8 of CYL770, with antibody titers comparable to one another and similar to those obtained on PS8 purified from the Becker or Wright strains. Despite these considerable differences, which may potentially be reflected by different immunogenic and antigenic properties, the inventors have demonstrated, by means of characterization and immunogenicity experiments, that the rPSs conserve, firstly, their characteristic primary structure as described by C. Jones (Carbohydr. Res., 2005, 340, 1097-1106) and conserve, secondly, the immunogenicity and the antigenicity of the wtPSs.

The inventors have in particular evaluated the cross reactivity of an anti-CYL770 serum against various *S. aureus* type 8 strains. For this, a hyperimmune serum was prepared in rabbits by injection of formolized whole microorganisms of the CYL770 strain, and adsorbed on chemically decapsulated autologous microorganisms. The results obtained show that the anti-CYL770 strain serum exhibits a cross reactivity with the wild-type Becker and Wright strains exhibiting a wtPS T8 at their surface. These results therefore demonstrate that it is possible to use the overproducing CYL770 strain to produce large amounts of a T8 capsular polysaccharide that can be used in an immunization method.

The rPSs can be produced by means of a method of production comprising the steps consisting in:
a) culturing an overproducing S. aureus strain, in particular a CYL1892 or CYL770 strain,
b) inactivating the culture thus produced, and
c) recovering the T5 or T8 capsular polysaccharide from the culture supernatant.

Step (a) can be carried out on a solid or liquid culture medium. Any culture medium described in the literature as being suitable for culturing a capsulated S. aureus strain can be used to do this. Mention may be made, by way of nonlimiting example, of the following media: TSB (trypticase soy broth); Poutrel defined medium (Poutrel et al., Clin Diagn Lab Immunol. 1995 2(2): 166-71); Columbia broth. Reference is subsequently made to inducing or noninducing media. The term "inducing medium" is intended to mean a culture medium which contains an element (for example, NaCl or another salt such as $CaCl_2$ and $MgCl_2$) which acts indirectly or directly on the inducible principal promoter of the cap locus. An inducing medium is therefore a medium capable of inducing the production of capsule in S. aureus strains comprising an inducible principal promoter in the cap locus. Conversely, a noninducing medium is a culture medium which does not contain such a signal.

In the context of the present invention, a medium free of protein of animal origin will preferably be used.

The term "protein of animal origin" is intended to mean proteins obtained from material of animal origin and also any product derived therefrom, such as derivatives derived from the chemical treatment of animal proteins. It is also intended to mean the products of partial or total hydrolysis of these animal proteins, such as peptones, polypeptides, peptides, or amino acids derived therefrom.

The culturing step can be carried out by inoculating the culture medium with an inoculum, for example with an initial $OD_{680\ nm}$ of 0.2, and incubation at 37° C. for a period, for example of approximately 48 to 72 hours, in an atmosphere possibly containing $CO_2$ at a concentration of 5 to 10% (for a T5 strain, without $CO_2$, and in the case of the use of a T8 strain, with $CO_2$). The culture volume can vary as required. Volumes of 400 ml to 20 l or larger volumes, for example from 30 l to 100 l, can be used. Preferably, a culture medium volume to culture container volume ratio of 20% (V/V) is maintained so as to promote oxygenation. For the large volumes, the oxygenation is verified and regulated in the course of the culturing by adjusting the oxygen pressure and appropriate agitation.

Depending on requirements, the culturing step can comprise successive cultures in increasing volumes in order to increase the biomass and the amount of polysaccharide which are produced. The culture resulting from step (a) is subsequently subjected to an inactivation step (b).

The inactivation step can be carried out by treatment of the culture with a phenol/ethanol (1V/1V) mixture at a rate of 2% by volume final concentration, and then agitation, for example using a magnetic bar, at ambient temperature for 6 hours to 48 hours depending on the biomass to be treated. The inactivation is verified by means of a mortality test. To do this, 100 microliters of the treated culture are plated out on a Columbia 2% NaCl agar and, in parallel, 100 microliters of the treated culture are inoculated into trypticase soy broth supplemented with $\frac{1}{30}^{th}$ of horse serum. The cultures are incubated for 48 hours at 37° C., the stoppers of the broth flasks remaining unscrewed. The absence of viable bacteria is reflected by an absence of growth after incubation for 24 hours at 37° C. Once the mortality of the culture has been established, the capsular polysaccharide is recovered.

In the case of the overproducing S. aureus strains, in particular CYL770 and CYL1892, the majority of the rPSs T8 and T5 is released into the culture supernatant. The rPSs can therefore be isolated directly from the latter. To do this, at the end of the inactivation step, the medium is centrifuged and the cell pellet is eliminated.

The rPS contained in the culture supernatant can then be purified by means of any conventional technique for purifying PS. Various purification techniques have been described in the literature and can be used in the context of the present invention. Reference may, for example, be made to the articles by Lee J. C. et al 1987; 55 2191-2197 or by Fattom et al Infect. Immun. 1990; 58 2367-2374, the latter describing a method involving release of the PSs with lysostaphin, and treatments with RNAse, DNAse, protease, fractionated ethanolic precipitation, ion exchange and molecular sieving. In the context of the present invention, a technique that produces an rPS exhibiting a degree of purity of at least 70% will preferably be used.

The physicochemical analyses and the one-dimensional proton nuclear magnetic resonance analysis at 500 MHz show that the rPSs T8 and T5 purified from an overproducing strain exhibit a structure in accordance with that described in the literature, with a degree of purity of at least 70% and a degree of O- and N-acetylation of greater than 70%. The residual products are present in the final product at a rate of less than 5% (w/w) of residual products of protein nature, less than 1% (w/w) of residual nucleic acids and less than 5% (w/w) of residual lipoteichoic acid and residual teichoic acid.

The amount of capsular polysaccharide obtained can be evaluated by means of the ELISA technique as described in example 1.

It has thus been shown that the CYL770 strain produces, in the supernatant, an amount of rPS T8 approximately 80 times greater than that produced by the parent Becker strain. This gain in productivity remains stable after successive passages in culture medium.

The inventors have, moreover, shown that the CYL1892 strain produces approximately 50 times more rPS T5, i.e. 200 µg/ml on average, than the parent wild-type strain. This gain in productivity has essentially been observed in the culture supernatant and remains stable after successive passages in culture medium. Moreover, the CYL1892 strain produces 7 times more T5 polysaccharide in the cell pellet than the wild-type parent strain.

Since some of the rPS T5 remains bound to the bacterial wall, the step consisting in recovering the rPS T5 can also comprise an additional step consisting in extracting the rPS T5 from the cells. Various extraction techniques have been described in the literature to do this, and can be used in the context of the present invention. Reference may, for example, be made to the articles by Lee J. C. Infect. Immun. 1993; 67: 1853-1858; Dassy B. et al. Gen. Microbiol. 1991; 137: 1155-1162 for a detailed description of these techniques.

The method of producing PS according to the invention can therefore be advantageously used for producing rPS T5, preferably from a CYL1892 strain, directly from the supernatant from extraction of the PS from the cell pellet. The method according to the invention therefore makes it possible to simplify the laborious steps of elimination of the numerous cellular contaminants, namely, for example: DNA, RNA, teichoic acid.

According to one embodiment, a subject of the invention is also an rPS capsular polysaccharide, in particular an rPS T5 of the S. aureus CYL1892 strain. Said polysaccharide is advantageously in isolated or purified form.

The rPSs T5 and T8 according to the invention can be fractionated or depolymerized, for example according to the method described in U.S. Pat. No. 6,045,805, to which reference may be made for a complete description of the operating conditions. In the context of the present invention, the terms "fractionate" and "depolymerized" are used without distinction. These fractionated rPSs are hereinafter referred to as rPSf. The rPSs T5 and T8 according to the invention are advantageously fractionated or depolymerized until an rPSf exhibiting an average molecular weight advantageously within a range of from 10 to 120 kDa, in particular within a range of from 30 to 70 kDa, is obtained, such as an rPSf of average MW of 50 kDa.

According to one embodiment, a subject of the invention is also therefore an rPSf capsular polysaccharide, in particular an rPSf T5, advantageously an rPSf T5 of the *S. aureus* CYL1892 strain. Said rPSf polysaccharide is advantageously in isolated or purified form.

The invention also relates to the use of the rPS T5 and T8 capsular polysaccharides produced by the overproducing *S. aureus* strains, advantageously the CYL1892 and CYL770 strains, for producing immunogenic compositions and vaccines for the treatment or prevention of infections with the *S. aureus* T5 and/or T8 strains.

The rPS capsular polysaccharides induce the production of antibodies that can mediate the destruction of the bacteria which carry them, by phagocytes in the presence of complement.

According to one embodiment, the invention therefore relates to an immunogenic or vaccine composition comprising an rPS T8 and/or T5 of an overproducing *S. aureus* strain, advantageously of a CYL770 or CYL1892 strain.

The invention also relates to the use of an rPS T8 and/or T5 of an overproducing *S. aureus* strain, advantageously of a CYL770 or CYL1892 strain, for the manufacture of an immunogenic composition or for the manufacture of a vaccine composition for use in the prevention and/or in the treatment of an *S. aureus* infection. In particular, said immunogenic or vaccine composition makes it possible to induce a humoral response against the *S. aureus* T8 and/or T5 strains in the individual to which it is administered.

According to a particular embodiment, said composition comprises the rPSs T8 and T5. Such an immunogenic or vaccine composition is particularly advantageous since it makes it possible to induce, in the individual to which it is administered, an immune response against the *S. aureus* T5 and T8 strains which represent the vast majority of infectious *S. aureus* strains.

The immunogenic or vaccine composition according to the invention can be used for combating the infections in infected individuals or preventing infection in individuals at risk, such as individuals who are hospitalized or who must undergo a surgical procedure.

When the immunogenic or vaccine composition according to the invention is intended for a child less than 2 years old or for an individual exhibiting a weakened immune defense, such as an elderly individual (>60 years old), the rPS according to the invention is preferably used in a conjugated form.

According to another embodiment, the present invention therefore relates to an rPS-carrier protein conjugate.

The term "carrier protein" is intended to mean a protein which allows cellular collaboration between T and B cells in the induction of the immune response against the capsular polysaccharide and thus improves the immunogenicity, whether for an active immunization or for a passive immunization using high-titer antisera prepared on volunteers. The carrier proteins are preferably proteins which are nontoxic and nonreactogenic. Nonlimiting examples of carrier proteins that can be used include recombinant or inactivated bacterial toxins such as *Pseudomonas aeruginosa* exotoxin A, tetanus toxoid, diphtheria toxoid or pertussis toxoid, Staphylococcal toxoids or exotoxins, or else *E. coli* thermolabile toxin (LT) or Shiga-toxins (ST). Bacterial outer membrane proteins can also be used, for instance the outer membrane complex c (OMPc), porins, transferrin-binding proteins, or pneumococcal surface protein A (PsaA). Other additional proteins, such as bovine serum albumin (BSA), keyhole limpet hemocyanin or tuberculin purified protein derivative (PPD) can be used as carrier protein.

Because of their high molecular weight, the rPS T5 et T8 polysaccharides are preferably "fractionated" or "depolymerized" before conjugation to the carrier molecule, for example according to the method described in U.S. Pat. No. 6,045,805 to which reference may be made for a description of the operating conditions to be used. Unfractionated rPSs can result in a lower cumulative conjugation and purification yield and in conjugates for which the sterilizing filtration can be more difficult to carry out due to their larger size. The depolymerized or fractionated rPSs are subsequently referred to in the application as rPSfs.

The rPSs according to the invention can be depolymerized or fractionated until rPSf exhibiting an average molecular weight of 10 to 120 kDa, in particular of 30 to 70 kDa, such as 50 kDa, is obtained. By way of illustration, the rPS T5 of the CYL1892 strain is depolymerized or fractionated until an rPSf having an average molecular weight advantageously within a range of from 30 to 70 kDa, for example 50 kDa, is obtained and the rPS T8 of the CYL770 strain is depolymerized or fractionated until an rPSf having an average molecular weight advantageously within a range of from 30 to 70 kDa, for example 50 kDa, is obtained.

The polysaccharide is subsequently functionalized before being conjugated to the carrier protein by covalent bonding. The functionalization can be carried out according to various methods. For example, activated carboxylate groups of the polysaccharide can be functionalized with adipic acid dihydrazide (ADH) or cystamine, and then the polysaccharide can be conjugated to the carrier protein by means of a carbodiimide-mediated reaction of the partially amidated polysaccharide with a carboxylate group of the carrier protein. Hydroxyl groups of the polysaccharide can also be activated using cyanogen bromide or 1-cyano-4-dimethylaminopyridium tetrafluoroborate, and then the polysaccharide can be functionalized with ADH in accordance with the method described by Kohn et al. (1993 FEBS Lett. 154: 209: 210). The functionalized polysaccharide is then bound to the carrier protein, for example to recombinant *Pseudomonas aeruginosa* exoprotein A in which the GLU 553 residue has been deleted, to which reference is made in the present application under the term rEPA, in the presence of ethyldimethylaminopropylcarbodiimide (EDAC). Size exclusion chromatography can then be used to separate the conjugates from the polysaccharides that have not reacted. The steps for activation of functionalization and conjugation do not impair the chemical structure of the repeating units of the polysaccharide.

According to one aspect, the invention therefore relates to a conjugate comprising PSf T8 and/or T5, advantageously of the CYL770 and CYL1892 strain, respectively, conjugated to a carrier protein, preferably the rEPA detoxified ExoA.

According to another aspect, the invention also relates to a conjugate comprising rPSf T8 and/or T5, advantageously of the CYL770 and CYL1892 strain, respectively, conjugated to a carrier protein, preferably the rEPA detoxified ExoA.

According to a specific embodiment, the invention relates to a mixture comprising the conjugates as defined above, in particular the PSf T8 and T5 conjugates or the rPS T8 and T5 conjugates, in which the PSs are conjugated to an identical or different carrier protein, advantageously identical and corresponding to the detoxified ExoA.

The conjugates according to the invention can be used for the manufacture of an immunogenic or vaccine composition, in particular a vaccine composition for use in the prevention and/or treatment of an S. aureus infection. The invention therefore also relates to an immunogenic or vaccine composition comprising said conjugates or a mixture thereof as defined above.

The compositions according to the invention are useful for inducing a humoral response in vivo, in particular for producing antibodies or antisera against an S. aureus T5 or T8 strain, or for combating the infection in infected individuals or preventing it in individuals at risk, such as individuals who have been hospitalized or who must undergo a surgical procedure.

A subject of the present invention is therefore also the preparation of said antibodies and antisera, which can be carried out by means of the conventional techniques for obtaining antisera and polyclonal or monoclonal antibodies well known to those skilled in the art, and also the directed antibodies and antisera thus produced.

The immunogenic or vaccine compositions according to the invention can be prepared by any usual method known to those skilled in the art. Usually, the antigens according to the invention are mixed with a pharmaceutically acceptable excipient. The term "pharmaceutically acceptable excipient" is intended to mean any excipient, filler, diluent, vehicle, preserving agent, etc., which is conventionally used in the preparation of compositions that can be administered to humans. In general, these products are selected according to the pharmaceutical form chosen and the route of administration and according to standard pharmaceutical practices. Reference may, for example, be made to Remington's Pharmaceutical Sciences, which constitutes a reference manual in the field.

The compositions according to the invention can also contain an adjuvant. Any pharmaceutically acceptable adjuvant or mixture of adjuvants conventionally used in the vaccines field can be used for this purpose. Mention may, by way of example of a suitable adjuvant, be made of aluminum salts, such as aluminum hydroxide or aluminum phosphate, DC-Chol and Toll agonists.

According to yet another aspect, the invention relates to a method of immunizing an individual against an S. aureus infection, comprising the administration to said individual of an immunologically effective amount of an immunogenic or vaccine composition according to the invention as described in the above description.

The term "individual" is intended to mean any individual at risk with respect to an S. aureus infection, such as, for example, an individual who has been hospitalized or who must undergo a surgical procedure.

The compositions according to the invention can be administered by any conventional route normally used in the vaccine field, such as the parenteral route (intravenous, intramuscular, subcutaneous, etc.). In the context of the present invention, for injectable compositions, an intramuscular administration will preferably be used. Such an administration can advantageously be performed in the muscles of the thigh or of the arm. The compositions according to the present invention can also be administered orally. An administration via the nasal, vaginal or rectal mucosa can also be recommended in the context of the present invention. The administration can be carried out through the administration of a single dose or of repeated doses. A vaccine dose can be prepared in a volume of 0.1 ml to 2 ml, preferably in a volume of 0.5 ml. An immunologically effective amount is an amount capable of inducing, in an immunized individual, a humoral response comprising antibodies capable of opsonizing an S. aureus strain and of facilitating its elimination by the phagocytes of the infected individual. The composition can be advantageously administered at least 10 to 14 days before the start of the period of increased risk of S. aureus infection.

The figures and examples below illustrate the invention without limiting the scope thereof.

FIGURES

FIG. 1 represents the amount of type 5 capsular polysaccharide (PS5) measured in the pellet or the culture supernatant for the Reynolds strain or the recombinant CYL1892 strain.

Figure 2:
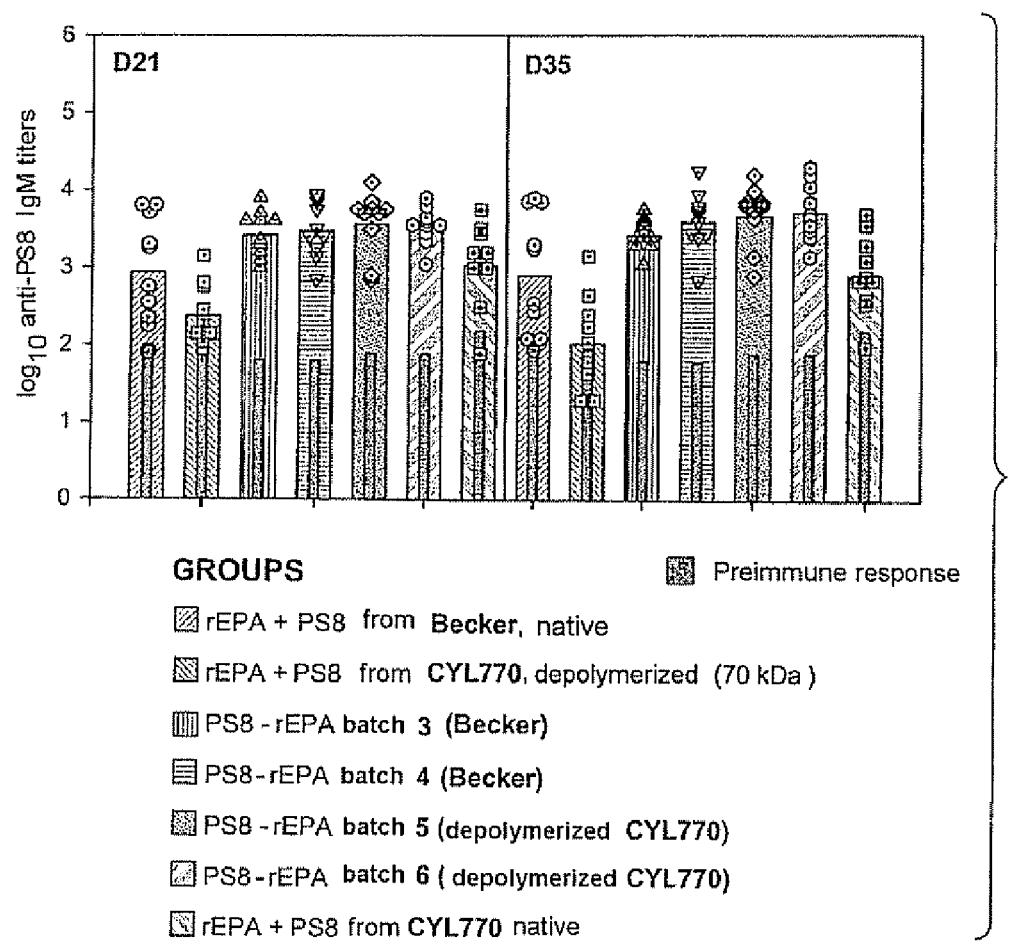

FIG. 2 represents the anti-PS8 IgM titers induced in mice immunized with the PS T8-rEPA conjugates prepared from the CYL770 strain or the Becker strain. The value of the titers (histogram) is represented by the Log of the mean of the inverses of dilution. For each of the groups, the individual titer of each serum (n=10) is represented by a symbol. The nonspecific response measured in the preimmune animals (D-1) is also represented.

Figure 3:
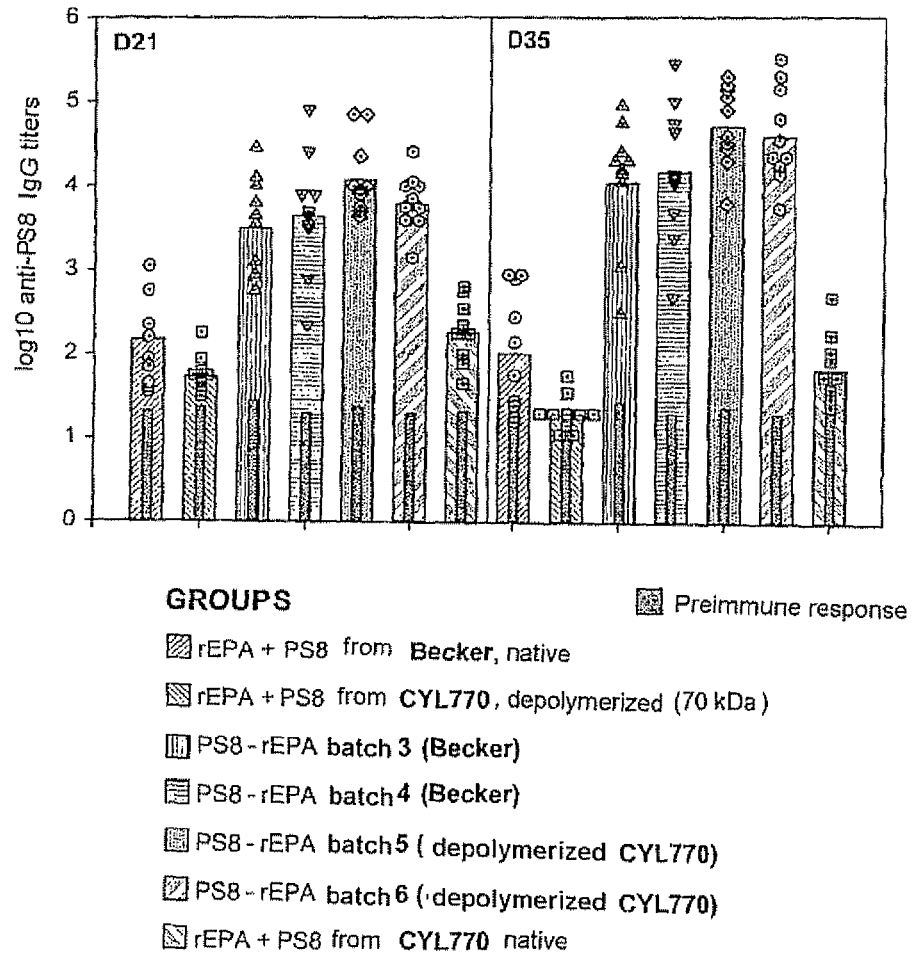

FIG. 3 represents the anti-PS8 total IgG titers induced in mice immunized with the PS T8-rEPA conjugates prepared from the CYL770 strain or the Becker strain. The value of the titers (histogram) is represented by the Log of the mean of the inverses of dilution. For each of the groups, the individual titer of each serum (n=10) is represented by a symbol. The nonspecific response measured in the preimmune animals (D-1) is also represented.

Figure 4:
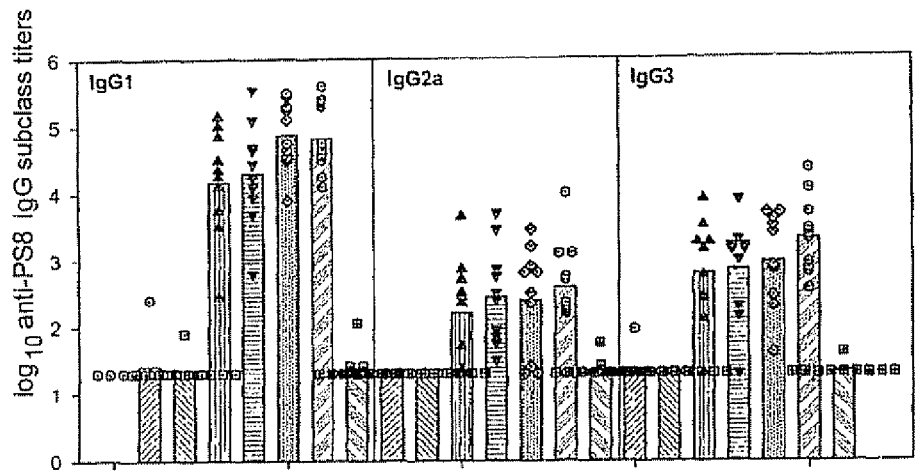

FIG. 4 represents the titers of the anti-PS8 IgG1, IgG2a and IgG3 subclasses, measured at D35 in mice immunized with the PS T8-rEPA conjugates prepared from the CYL770 or the Becker strain. The value of the titers (histogram) is represented by the Log of the mean of the inverses of dilution. For each of the groups, the individual titer of each serum (n=10) is represented by a symbol. The nonspecific response measured in the preimmune animals (D-1) is also represented.

Figure 5B:
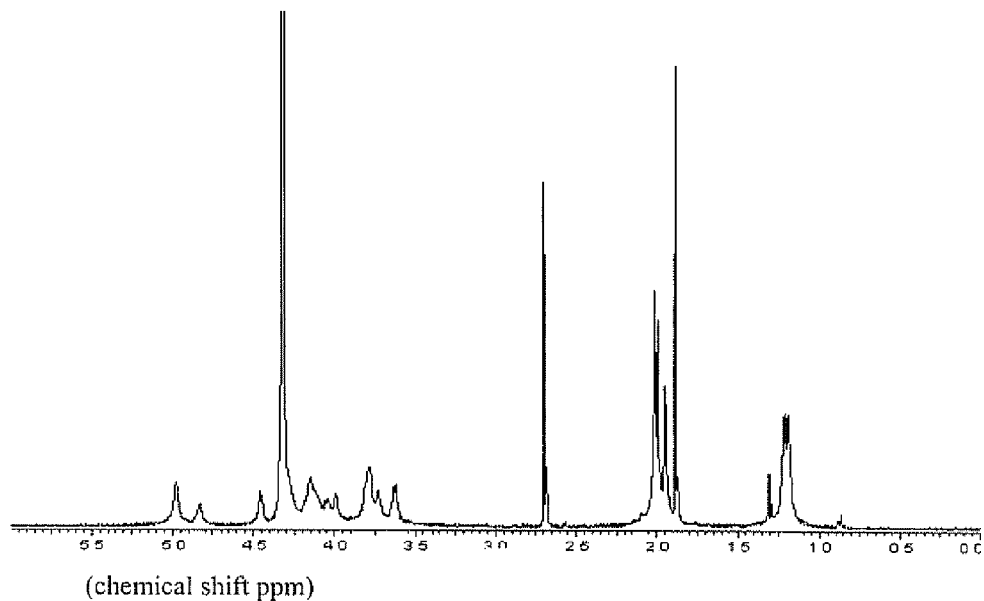
Figure 5B:
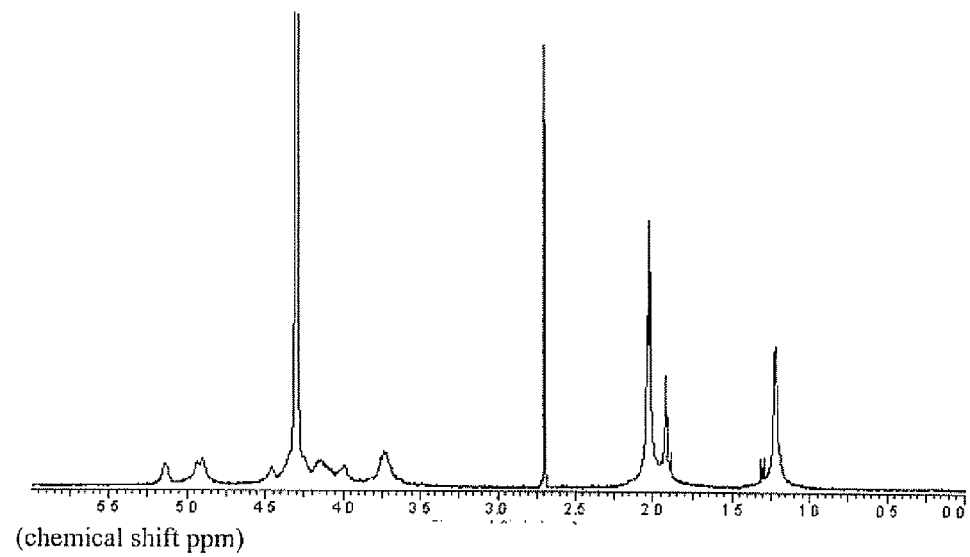

FIGS. 5(a) and (b) represent, respectively, the spectra obtained by one-dimensional proton NMR analysis at 500 MHz of the rPS8 polysaccharide purified from a supernatant of the CYL770 strain and of the wtPS8 purified from the cell pellet of a culture of the Becker strain. These NMR analyses were carried out using a Bruker DRX 500 spectrometer and a probe: BB-1H-D XYZ GRD 5 mm. The samples were taken up in $D_2O$ at a concentration of 1.2 mg/ml. The analysis was carried out under the following conditions: analysis temperature: 343° K (70° C.); relaxation time: 2 s; scanning number=512. For each PS8, the spectra were determined on the native (O-acetylated) form and on the de-O-acetylated form obtained by alkaline treatment as described by C. Jones (C. Jones. Carbohydr. Res. 2005, 340, 1097-1106).

Figure 6A:
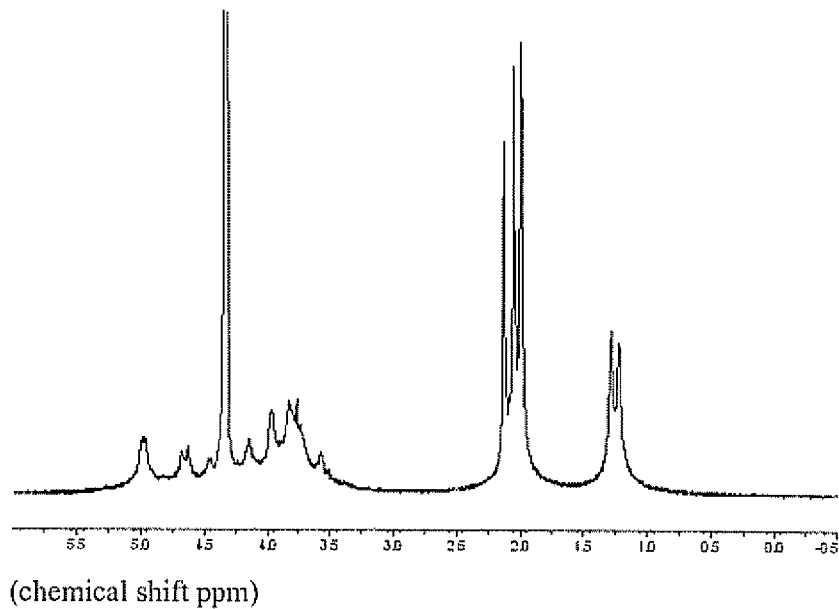
Figure 6B:
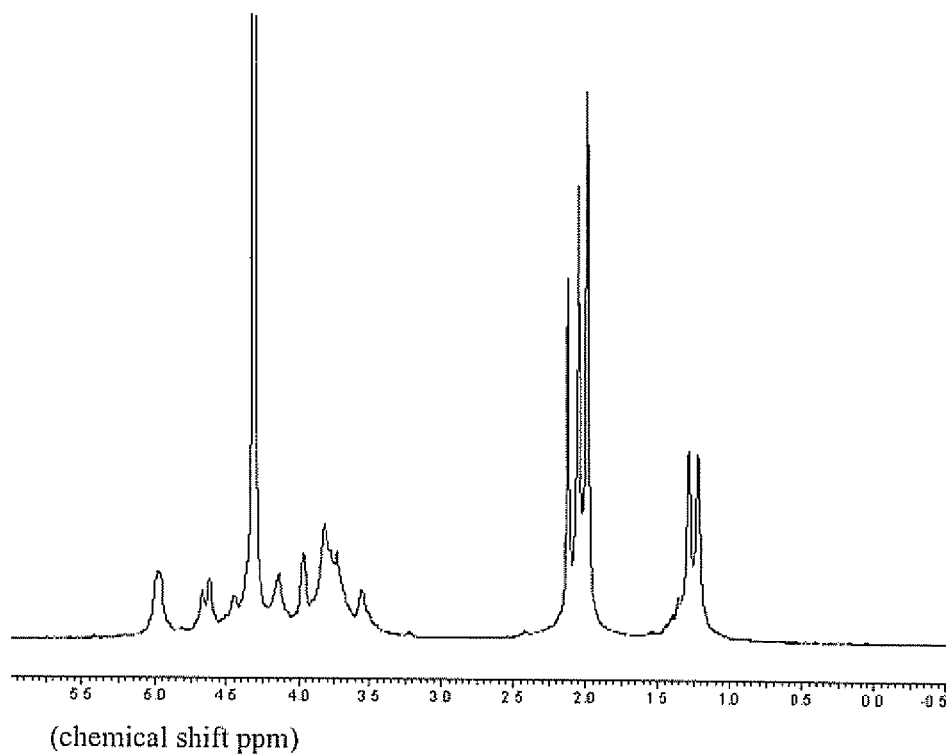

FIGS. 6(a) and (b) represent, respectively, the spectra obtained by one-dimensional proton NMR analysis at 500 MHz of the rPS5 polysaccharide purified from the culture supernatant of the CYL1892 strain and of the sPS5 purified from the cell pellet of a culture of the Reynolds strain. These NMR analyses were carried out using a Bruker DRX 500 spectrometer and a probe: BB-1H-D XYZ GRD 5 mm. The samples were taken up in $D_2O$ at a concentration of 1.2 mg/ml. The analysis was carried out under the following conditions: analysis temperature: 343° K. (70° C.); relaxation time: 2 s; scanning number=512.

FIGS. 7(a) and 7(b) represent, respectively, the evaluation and the comparison of the anti-PS5 IgM and IgG responses induced in mice with the PS5-rEPA and rPS5-rEPA conjugates.

EXAMPLES

The composition of the culture media used in the following examples is as defined in table 1 below. Said media were prepared by mixing the constituents in the order indicated in the table.

Preparation of the Frozen Materials of the Seed Batches A and B

Preparation of the Pre-Frozen-Materials

Cloning steps are carried out on noninducing M0 medium. An isolation is carried out on noninducing M0 medium, using an aliquot of 100 µl of the CYL1892 strain of origin. Two colonies are picked from this isolation, taken up with 50 µl of nuclease-free $H_2O$, and then inoculated again as isolated colonies. After three passages, one colony per dish is taken up and then inoculated as a layer (one colony uptake volume is sampled in parallel in order to perform a control by PCR). The layer thus obtained is then used for inoculating a 5-hour culture of inducing liquid M0 medium (50 ml). At the end of

TABLE 1

Preparation of the liquid and solid culture media

| Constituents | Concentration stock solution g/l | Inducing agar medium M0 Final conc. g/l | Volume per 37.5 ml in ml | Noninducing agar medium M0 Final conc. g/l | Volume per 37.5 ml in ml | Inducing liquid medium M0 Final conc. g/l | Volume per 100 ml in ml | Inducing medium M1 Final conc. g/l | Volume per 100 ml in ml |
|---|---|---|---|---|---|---|---|---|---|
| Wheat peptone | 387 | 3.87 | 1.5 | 3.87 | 1.5 | 30 | 7.75 | 30 | 7.75 |
| Yeast extract | 250 | 5 | 3 | 5 | 3 | 5 | 2 | 5 | 2 |
| D-glucose $H_2O$ | 100 | 1 | 1.5 | 1 | 1.5 | 1 | 1 | 1 | 1 |
| NaCl | 300 | 6 | 3 | 6 | 3 | 6 | 2 | 58.5 | 19.5 |
| $MgCl_2\, 6H_2O$ | 40 | 0.4 | 1.5 | 0.4 | 1.5 | 0.4 | 1 | 0.4 | 1 |
| $(NH_4)_2SO_4$ | 340 | 6.8 | 3 | | | 6.8 | 2 | 6.8 | 2 |
| $NH_4Cl$ | 300 | 6 | 3 | | | 6 | 2 | 6 | 2 |
| $FeCl_3\, 6H_2O$ | 12 | $120 \times 10^{-3}$ | 1.5 | $120 \times 10^{-3}$ | 1.5 | $120 \times 10^{-3}$ | 1 | $120 \times 10^{-3}$ | 1 |
| $ZnCl_2$ | 5 | $5 \times 10^{-3}$ | 0.15 | | | $5 \times 10^{-3}$ | 0.1 | $5 \times 10^{-3}$ | 0.1 |
| $CaCl_2\, 2H_2O$ | 10 | $10 \times 10^{-3}$ | 0.15 | | | $10 \times 10^{-3}$ | 0.1 | $10 \times 10^{-3}$ | 0.1 |
| Hepes 500 ml | 500 | | | 50 | 15 | | | | |
| $K_2HPO_4$ | 500 | | | 10 | 3 | | | | |
| KCl | 54 | | | 0.54 | 1.5 | | | | |
| $MnSO_4\, H_2O$ | 3.78 | | | $3.78 \times 10^{-3}$ | 0.15 | | | | |
| Ultrafiltered $H_2O$ | | | 19.2 | | 5.85 | | 81.05 | | 63.55 |
| TOTAL | | | 37.5 | | 37.5 | | 100 | | 100 |

Example 1

Characterization of the CYL1892 Type 5 Strain

A frozen material of the CYL1892 strain was provided by Dr. Chia Y. Lee (Arkansas University Medical Center, United States). It is the frozen material of origin.

Preparation of the Frozen Materials

Two types of frozen materials were prepared. Frozen material (A) is derived directly from the frozen material of origin by amplification on Columbia medium and contains, like the latter, materials of animal origin. A second frozen material (B) was derived from the frozen material of origin by cloning and repeated passages on medium free of materials of animal origin.

A preculture in TSB (trypticase soy broth) medium is inoculated using 100 µl of initial frozen material and placed at 37° C. for 18 hours with shaking. A culture of 400 ml is then inoculated using the preculture. After 5 hours at 37° C. with shaking, 200 ml of culture are added to 50 ml of glycerol filtered through 0.22 µm. The frozen materials are distributed into 100 tubes of 100 µl and 100 tubes of 1 ml and then stored at −80° C.

the culturing, the optical density at 680 nm is measured, and then 40 ml of culture are added to 10 ml of codified and 0.22 µm-filtered glycerol. The distribution is carried out in 45×1 ml and storage is at −80° C.

Culturing and Freezing of the Frozen Material B

Serial dilutions are prepared with the aim of eliminating all the components of animal origin possibly present in the frozen material of origin. The noninducing M0 medium is used in the passages.

The starting pre-frozen-material B is diluted to $\frac{1}{100}^{th}$ before the first passage on agar medium. Serial dilutions ($10^{-5}$) are then performed between each passage (passages 2 to 4). In total, four passages on agar medium were carried out, with a total dilution factor of $10^{-17}$. The layer corresponding to the final dilution performed is used to inoculate a culture of 400 ml of inducing liquid medium M0. The culture is stopped at the end of the exponential phase after 5 hours of culturing at 37° C. with shaking. $OD_{680\ nm}$ measurements are performed throughout the growth kinetics. The culture is then supplemented with glycerol at a final concentration of 20%, and then distributed into 6 Schott flasks kept in ice until the final distribution into tubes. The distribution is carried out as 1 ml in Nunc tubes and also as 5 ml in 15 ml Falcon tubes. The ampoules are then placed at −80° C.

Controls Performed

Viability

Counts are performed on each distribution flask at the time of distribution of the frozen materials B, before freezing, according to the protocol:

10-fold serial dilution in PBS, of the frozen materials, up to the dilution $10^{-9}$, deposition of 6 drops of 25 µl of the dilutions $10^{-3}$ to $10^{-9}$ on 24×24 Nunc dishes containing Columbia agar 2% NaCl, incubation at 37° C. for 18 hours, counting of the colonies in the most readable dilution range and calculation of the mean on the distribution flasks.

Viability controls were then carried out according to the same counting technique on several frozen materials corresponding to each distribution flask according to the plan: D+11 days, D+1 month, D+3 months, D+6 months, D+1 year.

Identity

The identity is verified using a frozen material, by means of the biochemical tests of the ApiStaph® system and a lysostaphin resistance test. These tests were carried out using an 18-hour culture at 37° C. on Columbia agar 2% NaCl and according to the indications given by the manufacturer.

Furthermore, capsular typing by T5/T8 multiplex PCR amplification is carried out using an isolation on Columbia agar 2% NaCl. The Reynolds and Becker strains are used as controls for the T5 and T8 amplifications.

A PCR test for cap1 genetic stability using the oligonucleotides Ppa1 NcoI and Ppa1r (described by Luong et al. in Infect. Immun. 2002; 70(7): 3389-95) is also carried out: an isolation is performed on Columbia agar 2% NaCl and incubated for 24 hours at 37° C. A colony is then recovered in order to carry out a second passage on Columbia agar 2% NaCl. Four successive passages are thus carried out. The DNA from the colonies is extracted in order to verify, by PCR, the presence of the cap1 promoter. The CYL770 strain is used as a control for the amplification of the cap1 promoter.

A verification of identity of the capsular polysaccharides of the T5 and T8 strains is carried out by means of an agglutination assay on a slide using specific monoclonal anti-PS5 (IgM) clone J1 and anti-PS8 (IgG1) clone K8-24 antibodies obtained from hybridomas provided by the Pasteur Institute, which were produced by conventional methods well known to those skilled in the art. The slide agglutination reactions were carried out using 50 µl of bacterial suspension adjusted to $OD_{680\,nm}=5$.

Evaluation of the Productivity by ELISA

Productivity Test

A preculture in inducing liquid medium M0 is inoculated using the frozen materials to be tested. A culture of 400 ml in inducing medium M1 is then inoculated and placed at 37° C. for 72 hours with shaking. At the end of the culturing, a volume of 50 ml of culture is removed and centrifuged for 30 minutes at 3500 rpm at +4° C. The capsular polysaccharides are subsequently extracted and then assayed by ELISA.

Stability Test

Successive cultures in medium M1 are performed so as to generate a number of generations similar to that which could be obtained in a 1000 liter fermenter. For this, 10 ml of M1 are inoculated with an ampoule of a frozen material B and then, after culturing for 16 h at 37° C., 8 successive cultures are performed by inoculating 10 ml of medium M1 at OD=0.2 and culturing, respectively, for 4 h, 4 h, 16 h, 4 h, 4 h, 16 h, 4 h and 4 h at 37° C. Using the last culture, 150 µl are inoculated onto an inducing agar medium M0 so as to perform a preculture at 37° C. for 16 h, and then 400 ml of M1 are inoculated at OD=0.2 and cultured for 72 h at 37° C. At the end of the final passage on medium M1, a productivity measurement is carried out as previously and compared with the productivity obtained for a reference frozen material under the same culture conditions.

Autoclave Extraction and Preparation of Samples

At the end of culturing, the suspensions are centrifuged for 30 minutes at 3500 rpm at +4° C., and the culture supernatants are separated and stored at +4° C. The pellets are extracted by means of two successive autoclaving cycles. Each cycle is composed of uptake of the pellets in 5 ml of PBS followed by a cycle of autoclaving for 60 minutes at 121° C. A mortality test is carried out on the autoclaved pellets by inoculation on Columbia agar 2% NaCl. The autoclaved pellets are subsequently centrifuged for 30 minutes at 25000×g at +4° C. and the extract (supernatant) is recovered and then stored at +4° C. The pellet is then again taken up in 5 ml of PBS and a second autoclaving cycle is initiated. At the end of the second cycle, the two extracts are combined. The extracts and culture supernatants are treated with proteinase K (50 µg/ml) for 1 hour at 37° C. and the proteinase K is then inactivated by incubation for 30 minutes at 80° C. A mortality test is then carried out on the treated culture supernatants.

PS5 ELISA Assay

The proteinase K-treated samples (extracts obtained after autoclaving and/or treated culture supernatants) are assayed by sandwich ELISA. A double titration makes it possible to be sure of the reliability of the data. The principle consists in capturing the antigen (PS5) between two antibodies so as to quantify it. In order to avoid any interference and to obtain as accurate a measurement as possible, one of the two antibodies must be completely specific (anti-PS5 monoclonal antibody used in adsorption). An adsorbed rabbit polyclonal serum is then used as detection antibody. A secondary antibody conjugated to peroxydase will allow the visualization. During the ELISA, a standard curve is realized with purified PS5, used at various concentrations so as to quantify the antigen. A control is also introduced; it is purified PS5, the concentration of which is known, and established by physicochemical measurement, to be 78 µg/ml. In the final step, a chromogenic substrate, tetramethylbenzidine (TMB), is added. The latter is degraded by the peroxydase to a blue-colored product. An acid is added after incubation for 15 minutes at 20° C. in the dark, which stops the reaction and converts the blue-colored product to yellow. The optical density is measured at 450 nm, it is proportional to the amount of antibody attached.

Results

CYL1892 Frozen Materials A

After freezing for 11 days, the CYL1892 count results are stable. Four successive passages were carried out. In total, 16 distinct colonies were extracted and analyzed by PCR. All the colonies tested at each passage clearly possess the type 5 cap locus, and the presence of the cap1 promoter was also demonstrated for all the colonies.

CYL1892 Frozen Materials B

After freezing for 11 days, the CYL1892 count results are stable ($2.3 \times 10^9$ CFU/ml on average).

Api System

A correct identification of *S. aureus* is obtained following the analysis of the biochemical characteristics according to the manufacturer's indications.

PCR Profile

The genetic stability of the pre-frozen-material was monitored during the various cloning steps. The presence of a specific amplification of cap5 at approximately 500 bp and of the cap1 promoter at 200 bp is noted. The ten colonies tested are derived from the pre-frozen-material B that was used for the inoculation of the culture for producing the frozen material B. Genetic stability of the cap5 loci and cap1 promoter is observed.

Twenty isolated colonies originating from the CYL1892 frozen material B were tested. The amplifications at approximately 500 bp and 200 bp illustrate the genetic stability of the cap5 loci and cap1 promoter.

Agglutination Assay

Only an agglutination with the anti-PS5 monoclonal antibody is observed.

Productivity of the CYL1892 Frozen Materials A and B (FIG. 1)

Productivity measurements were carried out several times in parallel with frozen material references and wild-type strain frozen materials. As for the recombinant strains, two types of frozen materials were prepared for the wild-type strains. A Reynolds frozen material A was obtained from the strain of origin by means of a small number of passages in the laboratory in Columbia broth 2% NaCl. This frozen material A contains materials of animal origin. A second frozen material (Reynolds frozen material B), free of material of animal origin, was obtained by successive passages of the strain of origin on media M0. The Reynolds frozen materials B were prepared in inducing liquid medium M0 after having undergone passages in noninducing medium M0.

It is observed that the recombinant CYL1892 strain produces, on average, 3.5 times more PS5 in the supernatant than in the pellet. The total amount thus produced represents approximately 10 times more PS5 compared with the wild-type Reynolds strain (300 µg/ml and 30 µg/ml, respectively) after culturing in inducing liquid medium M1. The difference is very significant in the supernatants. A PS5 production approximately 50 times greater for the CYL1892 strain compared with the wild-type Reynolds strain is observed. The difference is much less substantial with regard to the pellets. In fact, a 2-fold difference in PS5 productivity is observed for the CYL1892 strain compared with the Reynolds strain. It is noted that the CYL1892 frozen material B produces an equivalent amount of PS5 compared with the frozen material A.

Stability of the CYL1892 Frozen Materials A and B (FIG. 1)

Productivity measurements were carried out after a stability test on medium M1 (approximately 40 generations realized). The productivity observed in the pellets and supernatants after several passages in medium M1 is equivalent to that obtained without passage for the CYL1892 frozen material B as for the frozen material A. A 20 to 50% decrease in productivity is observed for the frozen materials B of the wild-type Reynolds strain.

The characterization of the recombinant *S. aureus* type 5 strain CYL1892 made it possible to observe that a gain in capsular polysaccharide productivity is obtained compared with the use of the wild-type Reynolds strain. Surprisingly, the difference in productivity was essentially observed in the culture supernatant (approximately 50x, i.e. 200 µg/ml on average) and remains stable after successive passages in inducing medium. These results show that the construct used to produce this recombinant strain is stable. The frozen materials A and B were therefore prepared from homogeneous populations.

Example 2

Characterization of the Type 5 Capsular Polysaccharide Produced by the CYL1892 Strain, and of the Type 8 Capsular Polysaccharide Produced by the CYL770 Strain The rPSs T8 and T5 isolated and purified from the CYL770 and CYL1892 strains, respectively, were characterized by means of the analyses described below.

A one-dimensional proton magnetic resonance analysis of purified rPS5 and purified rPS8 showed that these polysaccharides have the same primary structure as that already published (C Jones. Carbohydr. Res. 2005, 340, 1097-1106). This analysis makes it possible, in addition, to show directly that the rPS5 has a degree of N- and O-acetylation of greater than 70%. For the type 8 polysaccharide, the same analysis, carried out after de-O-acetylation of the antigen using NaOD added directly to the NMR tube, showed that the degree of N- and O-acetylation is greater than 70%. For the rPS5 and the rPS8, no non-identified or identified impurity of glycoside nature (such as peptidoglycan, teichoic acid, lipoteichoic acid, and antigen 336) that may have originated from *S. aureus* was detected by NMR analysis. The NMR spectra of the rPS8 and rPS5 purified from the CYL770 and CYL1892 strains, respectively, are given in FIGS. 5 et 6.

Steric exclusion high performance chromatography was carried out using a light scattering detector, a viscometer and a refractometer as on-line detectors. This analysis made it possible to evaluate the average molecular weights of rPS8 and rPS5 at 250 kDa and 150 kDa, respectively. These molecular weight values are higher than those of the capsular polysaccharides purified from the *S. aureus* Becker strain (type 8) or Reynolds strain (type 5) cultured with the same medium and under the same culture conditions and purified from the cell pellet (average molecular weight estimated at 150 kDa and 50 kDa, respectively).

Example 3

Preparation of an Anti-CYL770 Polyclonal Serum Adsorbed on Chemically Decapsulated Microorganisms and Evaluation of its Cross Reactivity on Various *S. aureus* Type 8 Strains A culture of the recombinant type 8 strain CYL770 was prepared in inducing medium M1. The microorganisms derived from this culture were formolized so as to be used for an immunization protocol in rabbits according to the principle described in the literature (Karakawa et al., 1985 *J Clin Microbiol* 22: 445-447). The hyperimmune serum obtained contains antibodies specific for the type 8 capsular polysaccharides, but also antibodies directed against other epitopes that may be common between the various strains. This serum was therefore adsorbed several times on pellets containing $10^{11}$ CFU of the autologous strain rendered chemically decapsulated so as to eliminate the antibodies not specific for the type 8 capsular polysaccharide. The reagent thus obtained was then evaluated by means of the technique of agglutination on whole microorganisms that have been trypsinized in order to avoid the nonspecific binding of the antibodies via protein A, on the microorganisms derived from cultures of the recombinant CYL770 strain in inducing medium M1. The anti-CYL770 serum was then tested under the same conditions on trypsinized whole microorganisms of the type 8 wild-type strains (Becker and Wright) derived from solid and liquid cultures having various levels of capsular polysaccharide induction.

Preparation of the CYL770 Microorganisms for Immunization

A preculture is prepared in an Erlenmeyer flask by inoculating an ampoule (1 ml) of CYL770 frozen material A in 9 ml of inducing liquid medium M0. The precultures are placed, with ×100 shaking, at 37° C. for 18 h to 20 h. The CYL770 strain is then cultured in an Erlenmeyer flask in 100 ml of M1, by inoculating at $OD_{680\,nm}$=0.2 using the preculture prepared in inducing liquid M0. The Erlenmeyer flask is then placed, with ×100 shaking, at 37° C. for 48 h. The culture is then centrifuged, the pellet is taken up with 20 ml of PBS (stock solution) and the $OD_{680\,nm}$ is measured.

A volume of stock solution is removed in order to perform the counting before formulation. From the sample of CYL770 stock solution, 10-fold dilutions are prepared in a 24-well plate, from $10^{-1}$ to $10^{-9}$. Six drops of 25 μl of each dilution are inoculated onto Columbia agar 2% NaCl and incubated for 18 to 20 h at 37° C. The CFUs are counted at the dilutions where this is possible and the number of CFU/ml (X) is determined according to the formula: X=(mean of CFUs per drop×40)/reading dilution. The determination of the equivalence OD/CFU (Y) is effected as follows: for $OD_{680\,nm}$=1, Y=(X/$OD_{680\,nm}$ stock solution).

The fixing with formol is carried out for 15 h by diluting a volume of CYL770 stock solution in PBS-3% formol so as to obtain 80 ml of suspension at $OD_{680\,nm}$=1.2, according to the protocol described by (Karakawa et al., 1985 *J Clin Microbiol* 22: 445-447). After treatment for 15 h, a mortality test is carried out by amplification of 1 ml of formolized suspension inoculated into 9 ml of TSB and placed, with ×100 shaking, at 37° C. for 18 to 20 h, and then inoculation of a mortality test on Columbia agar 2% NaCl by plating of 150 μl of the amplified culture as a layer and incubation for 18 to 20 h at 37° C.

The formol-treated microorganisms are then subjected to three successive washes with 1× concentrated phosphate buffer (PBS), pH 7, in order to eliminate the formol, centrifugation for 30 min at 3500 rpm at +4° C. (2×40 ml), washing with 2×40 ml, centrifugation for 30 min at 3500 rpm at +4° C., washing with 2×30 ml, centrifugation for 30 min at 3500 rpm at +4° C., washing with 2×20 ml (pool), centrifugation for 30 min at 3500 rpm at +4° C., and uptake of the microorganisms in PBS. The microorganism suspension thus treated can be stored at +4° C.

The formolized microorganisms are adjusted and aliquoted in 4 ml volumes in sterile 5 ml bottles. The adjustment of the suspensions of formolized microorganisms is carried out relative to the $OD_{680\,nm}$ values equivalent to the required microorganism concentrations:

2×4 ml at 6×10$^7$ CFU/ml (injections $d_2$+$d_4$)
4×4 ml at 1.2×10$^8$ CFU/ml (injections $d_0$+$d_7$+$d_9$+$d_{11}$)
3×4 ml at 1.8×10$^8$ CFU/ml (injections $d_{14}$+$d_{16}$+$d_{18}$)
3×4 ml at 2.4×10$^8$ CFU/ml (injections $d_{21}$+$d_{23}$+$d_{25}$)

The stoppers are inserted sterilely and the bottles are then crimped using pliers. The suspensions are stored at +4° C. for one week.

Preparation of the Chemically Uncapsulated Microorganisms for Adsorption

Using an ampoule of the frozen material A (1 ml) of the CYL770 strain, a preculture of 50 ml of Columbia medium is inoculated and incubated at 37° C. with shaking for 18 h. Using the preculture, a culture of 400 ml of Columbia medium is inoculated at an initial $OD_{680\,nm}$ of 0.2 and incubated at 37° C. with shaking for 24 h. The culture is then centrifuged at 3500 rpm for 30 min at +4° C. and the supernatant is eliminated. The pellet is then taken up with 8 ml of PBS and an OD measurement is carried out: $OD_{680\,nm}$=178.

The chemical treatment to be applied to the microorganisms in order to remove the capsular polysaccharides was described by Karakawa et al. (1985 Karakawa et al., 1985 *J Clin Microbiol* 22: 445-447). The following treatment is carried out in duplicate: 4 ml of bacterial suspension at OD=178 are transferred into a 250 ml glass Schott bottle, 30 ml of 0.2M glycine-0.14M HCl, pH 2, are added and the mixture is incubated for 20 min at exactly 100° C. (water bath). The suspension is transferred into 50 ml Falcon tubes and centrifuged at 3500 rpm for 30 min at +4° C., and the supernatant is eliminated. The pellets are washed 3 times with 40 ml of PBS. The pellets are then taken up and pooled with 30 ml of PBS and an OD measurement is carried out in order to determine the volume to be distributed per tube so as to have a total of $10^{11}$ CFU. After centrifugation at 3500 rpm for 30 min at +4° C. and elimination of the supernatant, the dry pellets are stored at −20° C. until use.

Adsorption of the Serum on Chemically Uncapsulated Microorganisms

Two ml of anti-CYL770 polyclonal serum were used for the adsorption protocol. A bacterial pellet of $10^{11}$ CFU makes it possible to carry out one adsorption cycle for 2 ml of serum. In total, 5 adsorption cycles were carried out, each cycle being composed in the following way: deposit 2 ml of decomplemented anti-CYL770 serum on a pellet of chemically uncapsulated microorganisms, resuspend gently, place on a rotary device for tubes at +4° C. for the day or overnight, centrifuge at 3500 rpm for 30 min at +4° C., recover the adsorbed serum, deposit the serum on a further pellet of chemically uncapsulated microorganisms and repeat the protocol. After the fifth cycle, the adsorbed serum is recovered and filtered through a 0.22 μm Millipore membrane, and then stored at +4° C. until its evaluation by means of a slide agglutination assay.

Agglutination Assay for the Adsorbed Serum

The slide agglutination assay for the anti-CYL770 polyclonal serum adsorbed on chemically uncapsulated microorganisms was carried out on trypsinized microorganisms derived from cultures, on various solid and liquid media, of the *S. aureus* type 8 strains (Becker, Wright and CYL770). A culture in solid medium not inducing PS of the *S. aureus* type 5 Reynolds strain was also tested as a control.

To prepare the trypsinized microorganisms, cultures in inducing agar solid medium M0 (for the type 8 strains) and Columbia medium with 2% NaCl (for the Reynolds strain) were prepared in the following way: 900 μl of PBS are added to 100 μl of frozen material of the Becker, Wright and Reynolds strains and 150 μl of bacterial suspension are plated out as a layer on a Petri dish and incubated at 37° C. for 18 h (37° C.+5% $CO_2$ for the Becker strain). The layers are then taken up in PBS and the suspensions are adjusted to $OD_{680\,nm}$=5.

For the Becker and Wright type 8 strains, liquid cultures of 50 ml in TSB medium and in medium M1 were prepared from solid precultures in TSB medium and inducing agar M0, respectively. The solid cultures were inoculated directly from a frozen material as described previously. The layers of the solid cultures were resuspended in PBS and were used to inoculate the liquid cultures at an initial $OD_{680\,nm}$ of 0.2.

For the recombinant CYL770 strain, a liquid culture of 50 ml in medium M1 was prepared. A preculture of 10 ml in inducing liquid medium M0 was directly inoculated using a frozen material of 1 ml. After incubation at 37° C. for 18 h with shaking, the culture medium M1 was inoculated at an initial $OD_{680\,nm}$ of 0.2 using the liquid preculture. The liquid cultures were incubated for 24 h at 37° C. with shaking. After culturing for 24 h, the $OD_{680\,nm}$ was measured and the cultures were centrifuged at 3500 rpm for 30 min at +4° C. The pellets were taken up in a volume of PBS necessary for adjusting the suspensions to $OD_{680\,nm}$=5.

The bacterial suspensions derived from the solid and liquid cultures and adjusted to $OD_{680\,nm}$=5 are treated with trypsin so as to eliminate any hindering trace of protein A. For this, 100 μl of trypsin at 50 mg/ml were added to an aliquot of bacterial suspension of 5 ml and the mixture was incubated for 1 h at 37° C. on a rotary device and then centrifuged at 3500 rpm for 30 min at +4° C. The pellets were washed 3 times with 5 ml of PBS and taken up with the volume of PBS necessary to adjust the suspensions to $OD_{680\,nm}$=5. The suspensions are stored at +4° C. until use.

The agglutination assays were carried out with 50 µl of trypsinized fresh microorganisms at $OD_{680\,nm}=5$. The microorganisms were plated out on the slide so as to completely cover the delimited glass circle intended for the agglutination without going outside it. A microorganism control was first of all prepared with 50 µl of suspension of microorganisms on which 5 µl of PBS were deposited. The control is validated in the absence of agglutination after 5 minutes of bringing into contact. A volume of 5 µl of anti-CYL770 polyclonal serum adsorbed on chemically decapsulated microorganisms was used for the agglutination assays. After deposition of the serum onto the slide in the three wells, the slide was agitated manually with a circular movement above a Kahn mirror (concave mirror). This step was timed from the addition of the serum to the first well.

Results

The CYL770 strain is cultured in medium M1 for 48 h, it is then fixed with formol. The direct mortality and also the mortality after amplification is verified. The suspension is then adjusted to the required concentrations (table 2) and distributed into sterile bottles. The bottles are then crimped and used for the immunization according to the protocol described in the literature (Karakawa et al., 1985 *J Clin Microbiol* 22: 445-447).

Agglutination of the Becker (except in TSB medium), Wright and CYL770 strains is observed with the adsorbed anti-CYL770 serum. Moreover, this serum does not allow agglutination of the control Reynolds microorganisms (type 5) cultured in Columbia agar 2% NaCl reference medium, nor of the Becker microorganisms cultured in TSB medium that does not induce PS8, thus demonstrating its specificity.

The adsorbed anti-CYL770 serum agglutinates the microorganisms all the more rapidly when the latter are carrying a type 8 capsule. The same agglutination profile is observed with the anti-PS8 monoclonal antibody (Mab-PS8).

The adsorbed anti-CYL770 serum therefore showed no difference in recognition on the three strains tested when the latter are placed under capsule-inducing conditions. Since the agglutination is related to the presence of capsular antigens, no difference between the type 8 capsular polysaccharides produced by these various strains is therefore to be noted.

TABLE 2

Concentration of formolized CYL770 microorganisms for immunization

| | Equivalence OD/CFU | Theoretical concentrations | | | Formolized microorganism solutions | |
|---|---|---|---|---|---|---|
| | CFU/ml for $OD_{680}=1$ | Volumes to be prepared | Desired final concentrations | Corresponding $OD_{680}$ values | Measured $OD_{680}$ values | Concentrations |
| CYL770 broth M1 | $1.06 \times 10^9$ | 10 | $6.0 \times 10^7$ | 0.038 | 0.040 | $6.2 \times 10^7$ |
| | | 20 | $1.2 \times 10^8$ | 0.077 | 0.079 | $1.2 \times 10^8$ |
| | | 15 | $1.8 \times 10^8$ | 0.115 | 0.115 | $1.8 \times 10^8$ |
| | | 5 | $2.4 \times 10^8$ | 0.154 | 0.159 | $2.5 \times 10^8$ |

Once produced, the serum is adsorbed on chemically uncapsulated autologous microorganisms and then evaluated against the type 8 strains by slide agglutination (table 3).

It therefore appears that the adsorbed anti-CYL770 serum thus produced allows a cross reactivity on the wild-type microorganisms exhibiting a type 8 capsule.

TABLE 3

Evaluation of the adsorbed anti-CYL770 serum by slide agglutination

| | Becker | | | | Wright | | | |
|---|---|---|---|---|---|---|---|---|
| | M0 inducing agar | M1 | TSB | CYL770 M1 | M0 inducing agar | M1 | TSB | Reynolds Columbia agar |
| PBS | − | − | − | − | − | − | − | − |
| Adsorbed anti-CYL770 serum | +++ | +++ | − | +++ | ++ | +++ | ++ | − |
| Mab-PS8 | ++(+) | +++ | − | ++++ | ++++ | ++++ | ++ | − |

The agglutination assay was read in the following way:
++++ complete agglutination observed in 0 to 30 sec
+++ complete agglutination observed in 30 sec to 1 min
++ complete agglutination observed in 1 to 3 min
+ complete agglutination observed in 3 to 5 min
+/− very slow and complete agglutination observed in 10 min
− no agglutination observed

Example 4

Generation of Anti-PS8 Polyclonal Antibodies in Rabbits Using the CYL770 Strain To characterize the nature of the PS8 produced by the CYL770 strain, anti-PS8 polyclonal antibodies were generated by immunization of rabbits with inactivated whole microorganisms of the CYL770 strain cultured in medium M1, using the protocol previously described by Karakawa and colleagues (Karakawa et al., 1985; J. Clin. Microbiol., 22: 445-447) as a basis.

Immunization Protocol

Injections: Three female New Zealand White rabbits (ESD—Charles River Laboratories, St Germain-sur-l'Arbresle, France) weighing 2.5 kg are injected 3 times a week for 4 weeks with various concentrations of inactivated whole microorganisms of the CYL770 strain cultured in medium M1 and dialyzed against PBS. The first injection (D0) is given subcutaneously in the scapular belt so as to avoid septic shocks. All the subsequent injections are given intravenously in the marginal ear vein. The concentrations and the volumes used for each of the injections are described below.

TABLE 4

Description of groups

| Groups | Antigen | Dilution buffer | Injection Route | Volume |
|---|---|---|---|---|
| 1:1 rabbit | PBS | 1X PBS, pH 7.2 | SC for the first injection IV for all the other injections | 1 ml |
| 2:2 rabbits | CYL770 in medium M1 0.6 to $2.4 \times 10^8$ CFU/rabbit | 1X PBS, pH 7.2 | SC for the first injection IV for all the other injections | 1 ml |

Composition of the 1X PBS, pH 7.2: 136 mM NaCl; 2.7 mM KCl; 8 mM $Na_2HPO_4$; 7.5 mM $KH_2PO_4$ Blood sample from the preimmune animals: five to 10 ml of blood are collected in Vacutainer™ tubes before the first immunization (D-1) for each rabbit, locally anesthetized with xylocaine, from the median artery of the ear. The samples are left to exudate for 3 h to 4 h at ambient temperature (20-22° C.) and then centrifuged at 4° C. for 20 min at 1500 g.

Blood sample by bleeding out: Samples are taken from all the animals by cardiac puncture under general anesthesia, 28 days after the first injection. Between 50 ml and 80 ml of blood are taken per animal and collected in sterile 50 ml Falcon™ tubes.

All the sera are conserved at −20° C. until use.

TABLE 5

Immunization scheme

| Week | Day | Injections | Interventions |
|---|---|---|---|
| | D-1 | — | Blood samples taken (10 ml/animal) |
| 1 | D0 | 1 ml, S.C. ($1.2 \times 10^8$ CFU) | Sensitization (1st injection, SC) |
| | D2 | 1 ml, I.V. ($6 \times 10^7$ CFU) | Amplification |
| | D4 | 1 ml, I.V. ($6 \times 10^7$ CFU) | Amplification |
| 2 | D7 | 1 ml, I.V. ($1.2 \times 10^8$ CFU) | Amplification |
| | D9 | 1 ml, I.V. ($1.2 \times 10^8$ CFU) | Amplification |
| | D11 | 1 ml, I.V. ($1.2 \times 10^8$ CFU) | Amplification |
| 3 | D14 | 1 ml, I.V. ($1.8 \times 10^8$ CFU) | Amplification |
| | D16 | 1 ml, I.V. ($1.8 \times 10^8$ CFU) | Amplification |
| | D18 | 1 ml, I.V. ($1.8 \times 10^8$ CFU) | Amplification |
| 4 | D21 | 1 ml, I.V. ($2.4 \times 10^8$ CFU) | Amplification |
| | D23 | 1 ml, I.V. ($2.4 \times 10^8$ CFU) | Amplification |
| | D25 | 1 ml, I.V. ($2.4 \times 10^8$ CFU) | Amplification |
| 5 | D28 | — | Bleeding out (50 ml to 80 ml/rabbit) |

Analyses of the Anti-PS8 Antibody Responses

The polyclonal rabbit sera are evaluated in terms of their specificity with respect to PS8 by means of an ELISA assay. 96-well ELISA plates (flat-bottomed microplates; Immunosorp Microwell; Nunc; Roskilde, Denmark) are incubated overnight at ambient temperature (20-22° C.) in the presence of 1 µg of purified PS8 per ml in 1×PBS, pH 7.2 (100 µl/well). The plates are washed 4 times with 300 µl/well of PBS/0.05% Tween 20 (PBS-Tween) using the Titertek M96V automatic plate washer, and are then saturated for 1 h at 37° C. with 250 µl/well of PBS-Tween/1% BSA. The plates are then washed 4 times according to the method described above. 100 µl per well of each of the sera to be tested at various concentrations are deposited onto the plate; the successive three-fold dilutions are prepared within the plate (column dilution), using a multichannel pipette, in PBS-Tween/1% BSA. The plates are incubated for 1 h 30 at 37° C. and then washed 4 times with PBS-Tween.

An HRP-conjugated anti-rabbit IgG conjugate (Southern Biochemicals Inc. Birmingham) is diluted to 1/12000 in PBS-Tween/1% BSA and 100 µl of the conjugate solution are added per well. The plates are incubated for 1 h 30 at 37° C. and then washed 4 times with PBS-Tween. For the visualization, 100 µl of the ready-to-use solution of TMB substrate (TEBU Bio-laboratories) are added per well and the plates are incubated for 15 min at ambient temperature (20-22° C.) in the dark. The enzymatic reaction due to the peroxidase is stopped by adding 100 µl of 1M $H_3PO_4$ per well. The optical density (OD) of each of the wells is measured at 450 nm using an automatic plate reader (Versamax). The background noise (average value on 4 blank wells) is subtracted from the measured OD values.

The specific anti-PS8 titers of the polyclonal antibodies correspond to the inverse of the arithmetic mean of the dilutions observed for two wells at 450 nm, relative to a reference serum.

TABLE 6

| | Anti-PS8 IgG titers | | |
| --- | --- | --- | --- |
| | Sera | | |
| | Becker M1 Positive control | CYL770 M1 | CYL770 M1 |
| anti-PS8 IgG titers | 30 000 | 8 500 | 5 000 |

Example 5

Production of Conjugates 5.1—Production of Type 8 Conjugates (STAPH8-rEPA)

Depolymerization of the Type 8 Polysaccharide Purified from the CYL770 Strain

Before its conjugation, the rPS8 antigen purified from the CYL770 strain is depolymerized according to the principle described in U.S. Pat. No. 6,045,805. The rPS8 antigen is prepared at 2 mg/ml. 110 µl of 200 mM ascorbic acid, 11 µl of 20 mM $CuSO_4$ and 11 µl of 20 mM $FeSO_4$ are added to 20 ml of this solution, at ambient temperature. The reaction is continued with stirring for 80 min at ambient temperature. The depolymerization reaction is stopped by adding 2 ml of a 2M solution of Tris at pH 7.0. The depolymerization reagents are removed by dialysis against water and then the depolymerized rPS8 is lyophilized. The average molecular mass of the depolymerized rPS8 was estimated at close to 50 kDa by HPSEC/LS/RI/Visc analysis.

Antigen Activation 40 mg of antigen (depolymerized for the polysaccharide purified from the CYL770 strain) were dissolved in 8 ml of 200 mM NaCl and of 125 mM adipic acid dihydrazide (ADH). The pH is adjusted to 4.9 and ethyldimethylaminopropylcarbodiimide (EDAC) is added at a final concentration of 25 mM. As the activation, which lasted 90 min at ambient temperature, progresses, the pH is constantly adjusted to a value of 4.9 by adding a dilute HCl solution. The reaction is stopped by neutralization of the pH. The activated antigen is then dialyzed against 500 mM NaCl and then against water. The activated and dialyzed antigen is then lyophilized. The percentage functionalization was estimated at 3.7 and 4.3 (w/w) for the polysaccharide purified from the Becker strain and for the polysaccharide purified and depolymerized from the CYL770 strain, respectively.

Antigen Conjugation

A solution of 10 ml containing 20 mg of the activated antigen (and depolymerized for the antigen purified from the CYL770 strain) and 10 or 20 mg of the carrier protein (recombinant exoprotein A Δ553, i.e. rEPA) in 100 mM NaCl and 50 mM EDAC was prepared. As the conjugation, which lasted 90 min at 4° C., progresses, the pH is constantly adjusted to a value of 5.6 by adding a dilute HCl solution. At the end of the reaction, the pH is neutralized. The conjugated antigen is then dialyzed against 200 mM NaCl and then purified by size exclusion chromatography on a sepharose Cl-4B column equilibrated with 200 mM NaCl in a 10 mM phosphate buffer, pH 7.2. The fractions which contained conjugates (as detected by optical absorption at 210 nm and 280 nm) and which are mainly eluted with the dead volume of the column, were combined.

Characterization of the Conjugated Antigen

After purification, the amounts of conjugated polysaccharide and protein were estimated as weight ratio of the polysaccharide (determined by quantification of O-acetyl according to the method of Hestrin (Hestrin S. 1949. J. Biol. Chem. 180: 249-261)) to the protein (determined by quantification of protein according to the Bradford method (Anal. Biochem. 1976 72, 248-254)). The level of nonconjugated antigen and of free carrier protein were determined by capillary electrophoresis. The size of the conjugate was estimated by HPSEC/LS/RI/Visc.

5.2—Production of Type 5 Conjugates (STAPH5-rEPA)

Depolymerization of the Type 5 Polysaccharide Purified from the CYL1892 Strain

Before its conjugation, the rPS5 antigen purified from the CYL1892 strain is depolymerized according to the principle described in U.S. Pat. No. 6,045,805. The rPS5 antigen is prepared at 2 mg/ml. 55 µl of 200 mM ascorbic acid, 5.5 µl of 20 mM $CuSO_4$ and 5.5 µl of 20 mM $FeSO_4$ are added to 20 ml of this solution, at ambient temperature. The reaction is continued with stirring for 80 min at ambient temperature. The depolymerization reaction is stopped by adding 2 ml of a 2M solution of Tris at pH 7.0. The depolymerization reagents are removed by dialysis against water and then the depolymerized rPS5 is lyophilized. The average molecular mass of the depolymerized rPS5 was estimated at close to 50 kDa by HPSEC/LS/RI/Visc analysis.

Antigen Activation 40 mg of antigen (depolymerized for the polysaccharide purified from the CYL1892 strain) were dissolved in 8 ml of 200 mM NaCl and of 50 mM adipic acid dihydrazide (ADH). The pH is adjusted to 4.9 and ethyldimethylaminopropylcarbodiimide (EDAC) is added at a final concentration of 10 mM. As the activation, which lasted 45 min at ambient temperature, progresses, the pH is constantly adjusted to a value of 4.9 by adding a dilute HCl solution. The reaction is stopped by neutralization of the pH. The activated antigen is then dialyzed against 500 mM NaCl and then against water. The activated and dialyzed antigen is then lyophilized. The percentage functionalization was estimated at 1.25 and 0.9 (w/w) for the polysaccharide purified from the Reynolds strain and for the polysaccharide purified and depolymerized from the CYL1892 strain, respectively.

Antigen Conjugation

A solution of 10 ml containing 20 mg of the activated antigen (and depolymerized for the antigen purified from CYL1892) and 40 mg of the carrier protein (recombinant exoprotein A, rEPA) in 100 mM NaCl and 50 mM EDAC was prepared. As the conjugation, which lasted 90 minutes at 4° C., progresses, the pH is constantly adjusted to a value of 5.6 by adding a dilute HCl solution. At the end of the reaction, the pH is neutralized. The conjugated antigen is then dialyzed against 200 mM NaCl and then purified by size exclusion chromatography on a sepharose Cl-4B column equilibrated with 200 mM NaCl in a 10 mM phosphate buffer, pH 7.2. The fractions which contained conjugates (as detected by optical absorption at 210 nm and 280 nm) and which are mainly eluted with the dead volume of the column, were combined.

Characterization of the Conjugated Antigen

After purification, the amounts of conjugated polysaccharide and protein were estimated as weight ratio of the polysaccharide (determined by quantification of O-acetyl according to the method of Hestrin (Hestrin S. 1949. J. Biol. Chem. 180: 249-261)) to the protein (determined by quantification of protein according to the Bradford method (Anal. Biochem. 1976 72, 248-254)). The level of nonconjugated antigen and of free carrier protein was determined by capillary electrophoresis. The size of the conjugate was estimated by HPSEC/LS/RI/Visc.

Example 6

Evaluation of the Immunogenicity of the Type 8 Conjugates (PS T8-rEPA) in Mice Various batches of PS T8-rEPA conjugates using PS8 purified from the Becker type 8 strain were generated by the authors. The immunogenicity of these type 8 conjugates could be demonstrated in various inbred or outbred mouse lines, by ELISA analysis of the anti-PS8 humoral response (IgM, IgG and subclasses of IgG). Dose-effect studies were also carried out on this type of animal model.

In order to demonstrate the immunogenicity induced by rPSfT8-rEPA conjugates generated using the PS8 purified from the recombinant CYL770 strain, animal tests and immunological analyses of the same type as those perfected for the type 8 conjugates having a Becker origin (wild-type strain) were developed and set up.

Immunization Protocol

Injections: Female OF1 mice (outbred) (ESD—Charles River Laboratories, St Germain-sur-l'Arbresle, France) weighing 20-22 g are injected subcutaneously in the scapular belt, at D0 (sensitization) and then 3 weeks after the first injection (D21), with various concentrations of PS T8-rEPA conjugates generated with PS8 derived from the CYL770 strain cultured in medium M1. The concentrations and the volumes used for each of the injections are described below.

TABLE 7

Description of the groups necessary (4 batches of conjugates) for a study to compare the immunogenicity induced by type 8 conjugates originating from the wild-type Becker strain or from the CYL770 strain.

| Groups | Designation | Antigen Dose/mouse | Dilution buffer | Injection Route | Volume |
|---|---|---|---|---|---|
| A | rEPA (2.5 µg/mouse) + purified wtPS8 from Becker (2.5 µg/mouse), nonconjugated | 2 × 2.5 µg | 0.9% NaCl | SC | 200 µl |
| B | rEPA (2.5 µg/mouse) + rPS8f from CYL770 (2.5 µg/mouse), nonconjugated | 2 × 2.5 µg | 0.9% NaCl | SC | 200 µl |
| C | PS8-rEPA batch 3 (wtPS8 from Becker) Prot/PS = 0.16 | 2 × 2.5 µg | 0.9% NaCl | SC | 200 µl |
| D | PS8-rEPA batch 4 (wtPS8 from Becker) Prot/Ps = 0.51 | 2 × 2.5 µg | 0.9% NaCl | SC | 200 µl |
| E | PS8-rEPA batch 5 (rPS8f from CYL770) Prot/PS = 0.69 | 2 × 2.5 µg | 0.9% NaCl | SC | 200 µl |
| F | PS8-rEPA batch 6 (rPS8f from CYL770) Prot/PS = 1.07 | 2 × 2.5 µg | 0.9% NaCl | SC | 200 µl |
| G | rEPA (2.5 µg/mouse) + rPS8 from CYL770 unfractionated (2.5 µg/mouse), nonconjugated | 2 × 2.5 µg | 0.9% NaCl | SC | 200 µl |

Prot/PS represents the final ratio after purification. It indicates the proportion of recombinant protein relative to the proportion of purified PS8 polysaccharide as weight/weight.

Intermediate blood samples: approximately 500 µl of blood are taken from the retroorbital sinus and collected in Vacutainer™ tubes in the preimmune animals, before sensitization ("prime") (D0) and then at D21, before amplification ("boost") for each of the mice. For the intermediate samples, the mice are anesthetized by intraperitoneal injection of 0.2 ml/mouse of a mixture of 8 mg/ml of Ketamine and 1.6 mg/ml of Xylazine.

Final blood sample by bleeding out: All the animals are bled out under general anesthetic at D35, two weeks after the amplification. Between 1 ml and 1.5 ml of blood are taken per animal and collected in Vacutainer™ tubes.

The blood samples are left to coagulate and to exudate for 3H at ambient temperature (20-22° C.), then centrifuged at 4° C. for 3 min at 6000 g and then transferred into Nunc 1 ml conical tubes, and the sera are conserved at −20° C. until use.

Analyses of the Antibody Responses

The anti-PS8 humoral response (anti-PS8 IgG and IgM titers at D0, D21 and D35, and anti-PS8 IgG1, IgG2a and IgG3 titers at D0 and D35 for the immunization doses determined within the assay) is evaluated by means of an ELISA assay using characterized PS8 purified from the Becker T8 strain as antigen for the adsorption ("coating") at a concentration of 1.5 µg/ml.

The PS8 purified from the Becker strain, and not that purified from the recombinant CYL770 strain, was chosen for the adsorption in order to evaluate the antibody response generated by the rPSfT8-rEPA conjugates (origin CYL770) against a wt PS8 purified from a "wild-type" strain. All the PS8-specific sera are analyzed by automated ELISA assay (Zymark robot) according to the following procedure.

96-well ELISA plates (M129B, Dynex) are incubated overnight at ambient temperature (20-22° C.) in the presence of 1 µg/ml of PS8 purified from the Becker strain in 1×PBS, pH 7.2 (100 µl/well). The plates are washed 4 times with 300 µl/well of PBS/0.05% Tween 20 (PBS-Tween) using the Titertek M96V automatic plate washer, and are then saturated for 1 h at 37° C. with 250 µl/well of PBS-Tween/1% BSA. The plates are washed 4 times according to the method described above. 100-µl per well of each of the sera to be tested at various concentrations are deposited onto the plate. The successive 2-fold dilutions are prepared within the plate itself (on-line dilution) in PBS-Tween/1% BSA. The plates are incubated for 1 h at 37° C. and then washed 4 times with PBS-Tween.

100 µl/well of anti-mouse Ig conjugate, diluted to the appropriate concentration according to the class of Ig, in PBS-Tween/1% BSA, are added and the plates are incubated for 1 h at 37° C. and then washed 4 times with PBS-Tween. For the visualization, 100 µl of the TMB solution are added per well and the plates are incubated for 20 min at ambient temperature (20-22° C.) in the dark. The enzymatic reaction due to the peroxidase is stopped by adding 100 µl of 1N HCl per well. The optical density (OD) of each of the wells is measured from 450 nm to 630 nm using an automatic plate reader (Labsystem). The background noise (average value on 4 blank wells) is subtracted from the measured OD values.

The anti-PS8 titers are calculated using the CodUnit software, for ODs for which the values range between 0.2 and 3, relative to the reference curve given by the standard serum which is present on each of the plates. The Ig titer of this standard, expressed in arbitrary ELISA units, was determined beforehand on a cumulation of several measurements and corresponds to the arithmetic mean of the inverses of the dilution for an $OD_{450\ nm}=1$. The detection threshold of this ELISA is evaluated at 10 ELISA units (1 $\log_{10}$). The titers of each serum are expressed as $\log_{10}$.

Results

Anti-PS8 IgM Titer

The results represented in FIG. 2 show that a significant but nonspecific anti-PS8 response is observed in all the preimmune animals (titer greater than 2 Log). After sensitization (D21), an marked increase in the specific anti-PS8 IgM response is observed for the 4 groups of conjugates (~+2 Log) and no difference is observed between these 4 groups. For the groups having received nonconjugated PS8, a marked increase in the anti-PS8 IgM titers, of approximately 1 Log for group A (Becker PS8+rEPA, nonconjugated) and of approximately 1.5 Log for group G (native PS8 from CYL770+rEPA, nonconjugated), is observed. No increase in the anti-PS8 IgM titers is observed for group B (fractionated PS8 from CYL770+rEPA, nonconjugated). At D35, there is no significant amplification effect on the IgM response whatever the group considered.

Anti-PS8 Total IgG Titer

The results represented in FIG. 3 show that no or very little nonspecific anti-PS8 IgG response is observed in the preimmune animals (<1.3 Log).

After sensitization (D21), a very strong specific anti-PS8 IgG response is observed for the 4 groups of conjugates (>+2.3 Log), with the response means between 3.5 Log and 4.1 Log. No difference is observed between the 4 groups of conjugates after sensitization. This anti-PS8 response is clearly greater than that obtained in the groups injected with the nonconjugated PSs. However, an increase in the anti-PS8 IgG titers at D21, of approximately 1 Log for group A (Becker PS8+rEPA, nonconjugated) and group G (native PS8 from CYL770+rEPA, nonconjugated), can be noted. No increase in the anti-PS8 IgG titers is observed for group B (fractionated PS8 from CYL770+rEPA, nonconjugated).

At D35, a significant amplifying effect is observed only for the 4 groups of conjugates, whatever the group considered (>+0.6 Log). The anti-PS8 response means are between 4.1 Log and 4.9 Log. When considering the response means, there is no significant difference between the conjugates derived from Becker and the conjugates derived from CYL770. However, it appears that the anti-PS8 response obtained with the conjugates derived from the CYL770 strain, evaluated on PS8 purified from the Becker wild-type strain, is more homogeneous within the same group.

Titers of the Anti-PS8 IgG1, IgG2a and Ig3 Subclasses, Measured at D35

FIG. 4 shows that no nonspecific anti-PS8 response is observed in the preimmune animals (<1.2 Log).

For the IgG1s, a very strong specific anti-PS8 response is observed for the 4 groups of conjugates (>4 Log), whereas no response is detected for the 3 groups having received the various types of nonconjugated polysaccharides. There is no significant difference in the response means between the Becker conjugates and the CYL770 conjugates, but it appears, however, that the response obtained with the two CYL770 conjugates is more homogeneous within the same group.

For the IgG2as, the response is slightly increased for the 4 groups of conjugates (between 2.5 Log and 2.8 Log), but, however, significant in comparison with the responses obtained with the groups immunized with the nonconjugated PSs.

For the IgG3s, a more marked IgG3 response is observed for the 4 batches of conjugates in comparison with the IgG2a response. No significant difference is observed between the various conjugates. The groups having received the nonconjugated PSs do not exhibit any anti-PS8 IgG3 response.

These results show that the PS8-rEPA conjugates, generated from purified PS8, derived from the Becker "wild-type" strain or from the recombinant CYL770 strain, induce strong specific anti-PS8 antibody responses in the OF1 mouse model, compared with the purified polysaccharides injected alone. A significant amplifying effect is also observed for these four batches of conjugates. This response is evaluated on PS8 purified from the Becker "wild-type" strain. From the point of view of the antibody response means, no significant difference is observed between the various batches of conjugates, whatever the origin of the PS8. However, it appears that the anti-PS8 total IgG and IgG1 responses, obtained with the conjugates derived from CYL770, are more homogeneous within the same group.

Example 7

Evaluation of the Immunogenicity of the Type 5 Conjugates (PS T5-rEPA) in Mice

Various batches of PS T5-rEPA conjugates were generated using PS5 purified from the Reynolds type 5 strain or rPS5 purified from the recombinant *Staphylococcus aureus* CYL1892 strain.

The immunogenicity of these type 5 conjugates could be demonstrated in mice by ELISA analysis of the anti-PS5 antibody response (total IgM and IgG). In order to compare the specific antibody responses induced, each of the conjugates was injected at an optimal immunization dose (defined beforehand in dose-effect studies) of 2.5 μg/mouse/injection).

Immunization Protocol

Injections: Female OF1 mice (outbred) (ESD-Charles River Laboratories, St Germain-sur-l'Arbresle, France) weighing 20-22 g are injected subcutaneously in the scapular belt, at D0 (sensitization) and then again at D21, 3 weeks after this first injection, with 2.5 μg/mouse/injection of PS T5-rEPA conjugates generated from purified PS5 derived from the Reynolds strain cultured in M1 medium or from purified rPS5f purified from the CYL1892 strain.

TABLE 8

Characteristics of the conjugates tested

| Designation | PS5-rEPA #7 | PS5-rEPA #11 | rPS5-rEPA #14 | rPS5-rEPA #15 |
| --- | --- | --- | --- | --- |
| Derivation | PS5 0273-AH III | PS5 0316-AH V | rPS5 0383F2 | rPS5 0383F2 |
| Ratio ADH/PS | 1.92% | 1.26% | 0.88% | 0.88% |
| Conjugation conditions | [PS5] = 2 mg/ml Ratio Prot/PS = 0.5 | [PS5] = 2 mg/ml Ratio Prot/PS = 2 | [PS5] = 2 mg/ml Ratio Prot/PS = 2.6 | [PS5] = 2 mg/ml Ratio Prot/PS = 2 |
| Purification | Diafiltration CL4B | Ultrafiltration | Diafiltration CL4B | Diafiltration CL4B |
| Prot (μg/ml) | 33 | 277 | | |
| PS (μg/ml) | 37 | 184 | | |
| Ratio Prot/PS | 0.89 | 1.51 | 4.5 | 4.1 |
| Mw (kDa) | 600 | 9000 | 14 000 | 11 000 |

TABLE 9

Descriptions of the groups necessary for comparison of the immunogenicity induced by type 5 conjugates of which the PSs originate from the wild-type Reynolds strain or from the recombinant CYL1892 strain

| Groups | Antigen Designation | Dose (PS5)/ mouse | Dilution buffer | Injection Route | Volume |
|---|---|---|---|---|---|
| A | rEPA 0265 (2.5 µg/mouse) + PS5 0316 (2.5 µg/mouse), nonconjugated | 2 × 2.5 µg | 0.9% NaCl | SC | 200 µl |
| B | rEPA 0265 (2.5 µg/mouse) + rPS5 0383F2 (2.5 µg/mouse), nonconjugated | 2 × 2.5 µg | 0.9% NaCl | SC | 200 µl |
| C | rPS5-rEPA #14 | 2 × 2.5 µg | 0.9% NaCl | SC | 200 µl |
| D | rPS5-rEPA #15 | 2 × 2.5 µg | 0.9% NaCl | SC | 200 µl |
| E | PS5-rEPA #11 | 2 × 2.5 µg | 0.9% NaCl | SC | 200 µl |
| F | PS5-rEPA #7 | 2 × 2.5 µg | 0.9% NaCl | SC | 200 µl |

Intermediate blood samples: approximately 200 µl of blood are taken from the retroorbital sinus and collected in Vacutainer™ tubes. These samples are taken at D0 in the preimmune animals, before sensitization, and at D21 before the amplification ("boost") for each of the mice individually. For the intermediate samples, the mice are anesthetized by intraperitoneal injection of 0.2 ml/mouse of a mixture of 8 mg/ml of Ketamine (Imalgene) and 1.6 mg/ml of Xylazine (Roumpun).

Final blood sample by bleeding out: All the animals are bled out by carotid section under general anesthesia at D35, two weeks after the day of the boost. Between 1 ml and 1.5 ml of blood are taken per animal and collected in Vacutainer™ tubes.

The blood samples are left to coagulate and to exude for 3H at 20° C.-22° C., centrifuged for 3 min at 6000 g, then transferred into Nunc 1 ml conical tubes. The sera are conserved at −20° C. until use.

Analysis of the Antibody Response

The anti-PS5 humoral response (anti-PS5 IgM and IgG titers at D0, D21 and D35) is evaluated by means of an automated ELISA assay using sPS5 purified from the Reynolds type 5 strain as antigen for the adsorption ("coating") at a concentration of 1 µg/ml.

The sPS5 purified from the Reynolds strain was chosen for the coating in order to evaluate whether the rPS5fT5-rEPA conjugates (origin CYL1892) are capable of inducing an antibody response capable of specifically recognizing sPS5 purified from a wild-type *Staphylococcus aureus* strain. All the PS5-specific sera are analyzed by an automated ELISA assay (Zymark robot) according to the procedure described below.

96-well ELISA plates (M129B, Dynex) are incubated overnight at ambient temperature (20-22° C.) in the presence of 1 µg/ml of sPS5 purified from the Reynolds strain in 1×PBS, pH 7.2 (100 µl/well). The plates are washed 4 times with 300 µl/well of PBS/0.05% Tween 20 (PBS-Tween) using the automatic plate washer (Titertek M96V washer) and then saturated for 1 h at 37° C. with 250 µl/well of PBS-Tween/1% BSA. The plates are washed 4 times according to the method described above. 100 µl per well of each of the sera are deposited onto the plate. The successive 2-fold dilutions of the sera are prepared within the plate itself (on-line dilution) in PBS-Tween/1% BSA. The plates are incubated for 1 h at 37° C. and then washed 4 times with PBS-Tween.

100 µl/well of anti-mouse Ig conjugate, diluted to the appropriate concentration according to the class of Ig, in PBS-Tween/1% BSA, are added and the plates are incubated for 1 h at 37° C. and then washed 4 times with PBS-Tween. For the visualization, 100 µl of the TMB solution are added per well and the plates are incubated for 20 min at ambient temperature (20-22° C.) in the dark. The enzymatic reaction due to peroxidase is stopped by adding 100 µl of 1N HCl per well. The optical density (OD) of each of the wells is measured from 450 nm to 630 nm using an automatic plate reader (Labsystem). The background noise (average value over 4 blank wells) is subtracted from the measured OD values.

The anti-PS5 titers are calculated using the CodUnit software, for ODs for which the values range between 0.2 and 3, relative to the reference curve given by the standard serum which is present on each of the plates. The Ig titer of this standard, expressed in arbitrary ELISA units, was determined beforehand on a cumulation of several measurements and corresponds to the arithmetic mean of the inverses of the dilution for an $OD_{450\ nm}=1$. The detection threshold of this ELISA is evaluated at 10 ELISA units (1 $\log_{10}$). The titers of each serum are expressed as $\log_{10}$.

Results: Anti-PS5 IgM Titers

The results represented in FIG. 7(a) show that a significant but nonspecific anti-PS5 response is observed in all the preimmune animals (mean value of the titers ~1.8 Log±0.2 Log).

The mice having been injected with purified PS5 or rPS5 not conjugated to rEPA exhibit an anti-PS5 IgM response that is weaker at D21 (−0.7 Log) and at D35 (−1.2 Log) than in the mice having been injected with conjugates.

A specific and significant response is observed for the 4 conjugates at D21 and at D35, with a mean titer value obtained of around 3.2 Log±0.2 Log and 4 Log±0.2 Log, respectively.

No significant difference was demonstrated between the various conjugates in terms of anti-PS5 IgM response at D21 and D35, therefore they exhibit an immunogenicity similar to that of the PS5-rEPA conjugates. In addition, the IgMs induced by the rPS5-rEPA conjugates are capable of specifically recognizing PS5 purified from a wild-type strain of type 5, such as the Reynolds strain.

Anti-PS5 IgG Titers

The results given in FIG. 7(b) show that no anti-PS5 IgG response is observed in the preimmune animals (mean value of titers<1.3 Log: detection threshold).

A significant anti-PS5 IgG response is observed at D21, for the groups of mice having been injected with one or other of the conjugates, with an average titer value evaluated at around 3.2 Log±0.2 Log. A very strong "boost" effect is observed at D35 for all the groups of mice having been injected with one or other of the conjugates, with a mean titer value evaluated at around 5 Log±0.2 Log.

In addition, no significant difference was demonstrated at D21, likewise at D35, between the 4 conjugates and therefore the rPS5-rEPA conjugates exhibit an immunogenicity similar to that of the PS5-rEPA conjugates. In addition, the IgGs induced by the rPS5-rEPA conjugates are capable of specifically recognizing PS5 purified from a wild-type strain of type 5, such as the Reynolds strain, in the same way as the specific IgGs induced by the PS5-rEPA conjugates.

The anti-PS5 IgM and IgG responses induced in the mice with the rPS5-rEPA conjugates (batches 14 and 15) are very similar to those induced by the PS5-rEPA conjugates (batches 11 and 7) after the prime and after the boost. In addition, these studies also made it possible to demonstrate that the rPS5-rEPA conjugates are capable of inducing high levels of anti-PS5 antibodies that strongly recognize PS5 purified from a wild-type strain such as the Reynolds strain of *S. aureus* and have an affinity for this antigen that is similar to that observed for the anti-PS5 antibodies induced by the PS5-rEPA conjugates.

What is claimed is:

1. A method of producing a *S. aureus* serotype T5 or T8 capsular polysaccharide, comprising:
   a) culturing an overproducing *S. aureus* serotype T5 or T8 cell strain in a culture medium,
   b) inactivating the cell culture thus produced,
   c) separating the inactivated cells from the inactivated cell culture supernatant, and
   d) recovering the T5 or T8 capsular polysaccharide from the inactivated cell culture supernatant.

2. The method as claimed in claim 1, in which the overproducing strain is the CYL1892 strain.

3. The method as claimed in claim 1, wherein the overproducing *S. aureus* T5 strain is a strain wherein the principal promoter of the cap 5 operon has been replaced by a strong principal promoter of another *S. aureus* strain.

4. The method as claimed in claim 3, wherein the strong principal promoter is the cap 1 promoter.

5. The method as claimed in claim 3, wherein the overproducing *S. aureus* strain is the CYL1892 strain.

6. A method of producing a conjugate comprising a *S. aureus* serotype T5 or a T8 capsular polysaccharide covalently bonded to a carrier protein, comprising:
   a) producing a T5 or a T8 capsular polysaccharide by,
      i) culturing an overproducing *S. aureus* serotype T5 or T8 cell strain in a culture medium,
      ii) inactivating the cell culture thus produced,
      iii) separating the inactivated cells from the inactivated cell culture supernatant, and
      iv) recovering the T5 or T8 capsular polysaccharide from the inactivated cell culture supernatant,
   b) purifying the recovered T5 or T8 polysaccharide,
   c) fractionating the purified T5 or T8 polysaccharide, and
   d) bonding covalently the fractionated T5 or T8 polysaccharide to a carrier protein.

7. The method according to claim 6, wherein the overproducing *S. aureus* T5 strain is a strain wherein the principal promoter of the cap 5 operon has been replaced by a strong principal promoter of another *S. aureus* strain.

8. The method as claimed in claim 7, wherein the strong principal promoter is the cap 1 promoter.

9. The method as claimed in claim 8, wherein the overproducing *S. aureus* strain is the CYL1892 strain.

10. The method according to claim 6, wherein the overproducing *S. aureus* T8 strain is a strain wherein the principal promoter of the cap 8 operon has been replaced by a strong principal promoter of another *S. aureus* strain.

11. The method as claimed in claim 10, wherein the strong principal promoter is the cap 1 promoter.

12. The method as claimed in claim 11, wherein the overproducing *S. aureus* strain is the CYL770 strain.

13. The method as claimed in claim 6, wherein the carrier protein is the exotoxin A of *Pseudomonas aeruginosa*.

14. The method of claim 6 wherein the molecular weight of the fractionated T5 or T8 polysaccharide is from 10 to 120 kDa.

15. The method of claim 6 wherein the molecular weight of the fractionated T5 or T8 polysaccharide is from 30 to 70 kDa.

16. The method of claim 6 wherein the average molecular weight of the fractionated T5 or T8 polysaccharide is 50 kDa.

17. The method as claimed in claim 1, wherein the overproducing *S. aureus* T8 strain is a strain wherein the principal promoter of the cap 8 operon has been replaced by a strong principal promoter of another *S. aureus* strain.

18. The method as claimed in claim 17, wherein the strong principal promoter is the cap 1 promoter.

19. The method as claimed in claim 18, wherein the overproducing *S. aureus* strain is the CYL770 strain.

* * * * *